United States Patent
Barth et al.

(10) Patent No.: US 7,297,710 B1
(45) Date of Patent: Nov. 20, 2007

(54) DERIVATIVES OF N-[(1,5-DIPHENYL-1H-PYRAZOL-3-YL) METHYL]SULFONAMIDE, THEIR PREPARATION AND THEIR APPLICATION IN THERAPEUTICS

(75) Inventors: Francis Barth, Saint Georges d'Orques (FR); Christian Congy, Saint Gely du Fesc (FR); Serge Martinez, Montpellier (FR); Philippe Pointeau, Saint Clement de Riviere (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/457,014

(22) Filed: Jul. 12, 2006

(51) Int. Cl.
*A61K 31/415* (2006.01)
*C07D 231/10* (2006.01)

(52) U.S. Cl. ............... 514/406; 548/356.1; 548/373.1; 548/375.1; 514/403

(58) Field of Classification Search ............. 548/356.1, 548/373.1, 375.1; 514/403, 406
See application file for complete search history.

(56) References Cited

FOREIGN PATENT DOCUMENTS

| EP | 0656354 | 6/1997 |
| FR | 2856683 | 12/2004 |
| FR | 2888236 A1 * | 1/2007 |
| WO | WO 2004/052864 | 6/2004 |

* cited by examiner

*Primary Examiner*—Golam M. M. Shameem
(74) *Attorney, Agent, or Firm*—Balaram Gupta

(57) ABSTRACT

The present invention relates to compounds corresponding to the formula (I):

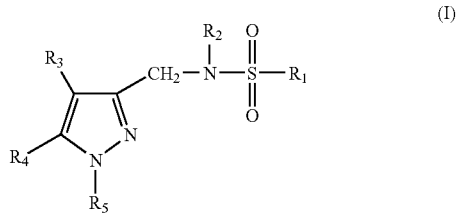

In which $R_1$, $R_2$, $R_3$, $R_4$ and $R_5$ are as described herein. The invention also relates to the method of preparation of said compounds and their application in therapeutics.

15 Claims, No Drawings

DERIVATIVES OF N-[(1,5-DIPHENYL-1H-PYRAZOL-3-YL)METHYL]SULFONAMIDE, THEIR PREPARATION AND THEIR APPLICATION IN THERAPEUTICS

BACKGROUND OF THE INVENTION

1. Field of the Invention

The present invention relates to derivatives of N-[(1,5-diphenyl-1H-pyrazol-3-yl)methyl]sulfonamide, their preparation and their application in therapeutics.

2. Description of the Art

Diphenylpyrazole derivatives displaying affinity for the $CB_1$ cannabinoid receptors were described notably in patents EP 0 576 357, EP 0 656 354 and U.S. Pat. No. 5,624,941, all of which are incorporated herein by reference in their entirety.

International patent application WO2005/073 197, which is incorporated herein by reference in its entirety, describes derivatives of N-[1,5-diphenyl-4-methyl-1H-pyrazol-3-yl)methyl]sulfonamide, antagonists of the $CB_1$ cannabinoid receptors.

Novel derivatives of N-[(1,5-diphenyl-1H-pyrazol-3-yl)methyl]sulfonamide have now been found which possess $CB_1$ cannabinoid receptor antagonist properties, localized at the central and/or peripheral level.

SUMMARY OF THE INVENTION

The present invention relates to compounds corresponding to the formula (I):

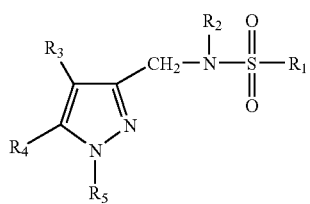

in which:

$R_1$ represents
- a $(C_1-C_{12})$alkyl, unsubstituted or substituted one or more times with substituents selected independently from a fluorine atom, a hydroxyl, a $(C_1-C_4)$alkoxy, a $(C_1-C_4)$alkylthio, a phenoxy, a trifluoromethoxy radical, a difluoromethoxy radical, a difluoromethylthio radical, a trifluoromethylthio radical;
- a non-aromatic $(C_3-C_{12})$ carbocyclic radical, unsubstituted or substituted one or more times with substituents selected independently from a $(C_1-C_4)$alkyl, a $(C_1-C_4)$alkoxy, a $(C_1-C_4)$alkylthio, a fluorine atom, a hydroxyl, a trifluoromethyl, difluoromethyl, trifluoromethoxy, difluoromethoxy, trifluoromethylthio, difluoromethylthio radical;
- a methyl substituted with a non-aromatic $(C_3-C_{12})$ carbocyclic radical, unsubstituted or substituted one or more times with substituents selected independently from a $(C_1-C_4)$alkyl, a $(C_1-C_4)$alkoxy, a $(C_1-C_4)$alkylthio, a fluorine atom, a hydroxyl, a trifluoromethyl, difluoromethyl, trifluoromethoxy, difluoromethoxy, trifluoromethylthio, difluoromethylthio radical;
- a phenyl, benzyl, benzhydryl, or benzhydrylmethyl radical, in which each phenyl group is unsubstituted or substituted one or more times with substituents selected independently from a halogen atom, a hydroxyl, a methylenedioxy, a cyano, a nitro, a $(C_1-C_4)$alkylcarbonyl group or an Alk, OAlk, $S(O)_n$Alk or $OS(O)_n$Alk group;
- a phenyl radical substituted with a heterocyclic radical selected from pyrrolyl, imidazolyl, pyridyl or pyrazolyl, said heterocyclic radical being unsubstituted or substituted one or more times with one or more substituents selected independently from a halogen atom or a $(C_1-C_4)$alkyl group;
- a phenyl radical substituted with a phenyl or a phenoxy in which each phenyl group is unsubstituted or substituted one or more times with substituents selected independently from a halogen atom, a hydroxyl, a methylenedioxy, a cyano, a nitro, a $(C_1-C_4)$alkylcarbonyl group or an Alk, OAlk, $S(O)_n$Alk or $OS(O)_n$Alk group;
- a thienyl, furyl, oxazolyl, thiazolyl, imidazolyl, pyrrolyl, or pyridyl group, said radical being unsubstituted or substituted with one or more substituents selected independently from a halogen atom, a $(C_1-C_4)$alkyl, a trifluoromethyl group;
- a tetrahydronaphthalenyl or a naphthyl unsubstituted or substituted with one or more substituents selected independently from a halogen atom, a $(C_1-C_4)$alkyl, a di$(C_1-C_4)$alkylamino or a trifluoromethyl group;
- a 2,3-dihydrobenzofuranyl unsubstituted or substituted one or more times with a $(C_1-C_4)$alkyl group;
- an indol-2-yl or an N-methylindol-2-yl;

$R_2$ represents a hydrogen atom, a $(C_1-C_4)$alkyl or a $(C_1-C_4)$alkylsulfonyl group;

$R_3$ represents a cyano, a hydroxyl, a $(C_1-C_4)$alkoxy, a cyanomethyl, a hydroxymethyl, a $(C_1-C_4)$alkoxymethyl, a fluoromethyl, a tetrazolylmethyl, an N-(methyl)tetrazolylmethyl, a tetrazolyl, an N-(methyl)tetrazolyl, a $CONR_6R_7$ group, a $CH_2S(O)_n(C_1-C_4)$alkyl group, a $COOR_8$ group or a $CH_2NR_6R_7$ group;

$R_4$ and $R_5$ each represent independently a phenyl, unsubstituted or substituted with one or more substituents selected independently from a halogen atom, a $(C_1-C_7)$ alkyl group unsubstituted or substituted one or more times with a fluorine atom, an OAlk, $S(O)_n$Alk or $OS(O)_n$Alk group;

$R_6$ and $R_7$ each represent independently a hydrogen atom or a $(C_1-C_4)$alkyl or $R_6$ and $R_7$ together with the nitrogen atom to which they are bound constitute a heterocyclic radical selected from pyrrolidinyl, piperidinyl, morpholinyl, piperazinyl unsubstituted or substituted one or more times with a $(C_1-C_4)$alkyl;

$R_8$ represents a $(C_1-C_4)$alkyl;

n represents 0, 1 or 2;

Alk represents a $(C_1-C_4)$alkyl unsubstituted or substituted one or more times with a fluorine atom.

DETAILED DESCRIPTION OF THE INVENTION

The compounds of formula (I) can contain one or more asymmetric carbon atoms. They can therefore be in the form of enantiomers or of diastereoisomers. These enantiomers, diastereoisomers as well as mixtures thereof, including the racemic mixtures, form part of the invention.

The compounds of formula (I) can be in the form of bases or of salts of addition to acids. Such salts of addition form part of the invention.

These salts are advantageously prepared with pharmaceutically acceptable acids but the salts of other acids that can be used for the purification or isolation of the compounds of formula (I) also form part of the invention.

The compounds of formula (I) as well as the salts of said compounds referred to hereinabove can also be in the form of hydrates or of solvates, i.e. in the form of associations or of combinations with one or more water molecules or with a solvent. Such hydrates and solvates also form part of the invention.

"Halogen atom" means an atom of bromine, of chlorine, of fluorine or of iodine.

"$(C_1-C_4)$alkyl or respectively $(C_1-C_7)$alkyl or $(C_1-C_{12})$alkyl" means a linear or branched alkyl radical of one to four carbon atoms or respectively of one to seven or of one to twelve carbon atoms, such as the methyl, ethyl, propyl, isopropyl, butyl, isobutyl, sec-butyl, tert-butyl, pentyl, isopentyl, hexyl, isohexyl, heptyl, etc. radical.

"$(C_1-C_4)$alkyl substituted one or more times with a fluorine atom" means in particular the difluoromethyl, trifluoromethyl, difluoromethyl, trifluoroethyl groups.

"$(C_1-C_4)$alkoxy or respectively $(C_1-C_5)$alkoxy" means a linear or branched alkoxy radical of one to four carbon atoms or respectively of one to five carbon atoms, such as the methoxy, ethoxy, propoxy, isopropoxy, butoxy, sec-butoxy, tert-butoxy radical.

"$(C_3-C_7)$cycloalkyl" means a cyclic alkyl group of 3 to 7 carbon atoms, such as the cyclopropyl, cyclobutyl, cyclopentyl, cyclohexyl, cycloheptyl group.

"Tetrazolyl" means a tetrazol-1-yl, tetrazol-2-yl or tetrazol-5-yl radical.

More particularly, the present invention relates to compounds corresponding to formula (I):

in which:
$R_1$ represents
 a $(C_1-C_7)$alkyl;
 a $(C_3-C_7)$cycloalkyl unsubstituted or substituted one or more times with a $(C_1-C_4)$alkyl group;
 a $(C_3-C_7)$cycloalkylmethyl unsubstituted or substituted one or more times on the carbocycle with a $(C_1-C_4)$alkyl;
 a phenyl unsubstituted or substituted with one or more substituents selected independently from a halogen atom, a $(C_1-C_4)$alkyl, a $(C_1-C_4)$alkoxy, a cyano, a trifluoromethyl group, a trifluoromethoxy group, an $S(O)_n$Alk group, a $(C_1-C_4)$alkylcarbonyl group, a phenyl;
 a benzyl unsubstituted or substituted with one or more substituents selected independently from a halogen atom, a $(C_1-C_4)$alkyl, a $(C_1-C_4)$alkoxy; a trifluoromethyl group;
 a thienyl, furyl, oxazolyl, thiazolyl, imidazolyl radical, said radical being unsubstituted or substituted with one or more substituents selected independently from a halogen atom, a $(C_1-C_4)$alkyl, a trifluoromethyl group;
 a naphthyl unsubstituted or substituted with one or more substituents selected independently from a $(C_1-C_4)$alkyl, a di$(C_1-C_4)$alkylamino;
 a 2,3-dihydrobenzofuranyl unsubstituted or substituted one or more times with a $(C_1-C_4)$alkyl group;
$R_2$ represents a hydrogen atom or a $(C_1-C_4)$alkyl;

$R_3$ represents a cyano, a hydroxyl, a $(C_1-C_4)$alkoxy, a cyanomethyl, a hydroxymethyl, a $(C_1-C_4)$alkoxymethyl, a fluoromethyl, a tetrazolylmethyl, an N-(methyl)tetrazolylmethyl, a tetrazolyl, an N-(methyl)tetrazolyl, a $CONR_6R_7$ group, a $CH_2S(O)_n$Alk group, a $COOR_8$ group;

$R_4$ and $R_5$ each represent independently a phenyl unsubstituted or substituted with one or more substituents selected independently from a halogen atom, a $(C_1-C_7)$alkyl, a $(C_1-C_4)$alkoxy, a trifluoromethyl group or an $S(O)_n$Alk group;

$R_6$ and $R_7$ each represent independently a hydrogen atom or a $(C_1-C_4)$alkyl or $R_6$ and $R_7$ together with the nitrogen atom to which they are bound constitute a heterocyclic radical selected from pyrrolidinyl, piperidinyl, morpholinyl, piperazinyl unsubstituted or substituted one or more times with a $(C_1-C_4)$alkyl;

$R_8$ represents a $(C_1-C_4)$alkyl;

n represents 0, 1 or 2;

Alk represents a $(C_1-C_4)$alkyl.

Among the compounds of formula (I) according to the invention, a distinction is made between:
 the compounds of formula $I_A$ in which $R_3$ is a cyano;
 the compounds of formula $I_B$ in which $R_3$ is a hydroxyl;
 the compounds of formula $I_C$ in which $R_3$ is a $(C_1-C_4)$alkoxy;
 the compounds of formula $I_D$ in which $R_3$ is a cyanomethyl;
 the compounds of formula $I_E$ in which $R_3$ is a hydroxymethyl;
 the compounds of formula $I_F$ in which $R_3$ is a $(C_1-C_4)$alkoxymethyl;
 the compounds of formula $I_G$ in which $R_3$ is a fluoromethyl;
 the compounds of formula $I_H$ in which $R_3$ is a $CH_2S(O)_n$Alk group;
 the compounds of formula $I_I$ in which $R_3$ is a $CONR_6R_7$ group;
 the compounds of formula $I_J$ in which $R_3$ is a $COOR_8$;
 the compounds of formula $I_K$ in which $R_3$ is a tetrazol-5-yl;
 the compounds of formula $I_L$ in which $R_3$ is an N-(methyl)tetrazol-5-yl;
 the compounds of formula $I_M$ in which $R_3$ is a tetrazol-5-ylmethyl;
 the compounds of formula $I_N$ in which $R_3$ is an N-(methyl)tetrazol-5-ylmethyl;
 the compounds of formula $I_O$ in which $R_3$ is a tetrazol-1-ylmethyl or a tetrazol-2-ylmethyl;
 the compounds of formula $I_P$ in which $R_3$ is a $CH_2NR_6R_7$ group;
 the groups Alk, $R_6$, $R_7$ and $R_8$ being as defined below for (I).

Preferred, among the compounds of formula (I) that are objects of the invention, are compounds in which:
$R_1$ represents:
 a phenyl, benzyl, benzhydryl, benzhydrylmethyl radical, in which each phenyl group is unsubstituted or substituted one or more times with substituents selected independently from a halogen atom, a hydroxyl, a $(C_1-C_4)$alkyl, a $(C_1-C_4)$alkoxy, a methylenedioxy, a cyano, a nitro, a trifluoromethyl, a difluoromethyl, a difluoromethoxy, a trifluoromethoxy, a trifluoromethylthio, a difluoromethylthio, an $S(O)_nAlk$ group, an $OS(O)_nAlk$ group, a $(C_1-C_4)$alkylcarbonyl group;

a furyl radical unsubstituted or substituted with one or more substituents selected independently from a halogen atom, a $(C_1-C_4)$alkyl, a trifluoromethyl group;

$R_2$ represents a hydrogen atom or a $(C_1-C_4)$alkylsulphonyl group;

$R_3$ represents a cyano, a hydroxyl, a $(C_1-C_4)$alkoxy, a hydroxymethyl, a $(C_1-C_4)$alkoxymethyl, a $CONR_6R_7$ group, a $COOR_8$ group, a tetrazol-1-yl methyl or a tetrazol-2-ylmethyl, the groups $R_6$, $R_7$, $R_8$ being as defined for (I);

$R_4$ represents a 4-chlorophenyl, a 4-methoxyphenyl or a 4-$OSO_2$-Alk, Alk representing a $(C_1-C_4)$alkyl unsubstituted or substituted one or more times with a fluorine atom;

$R_5$ represents a 2-chlorophenyl, a 2-bromophenyl or a 2,4-dichlorophenyl; in the form of a base or of a salt of addition to acids as well as in the form of hydrates or of solvates.

More particularly, the compounds of formula (I) are preferred in which:

$R_1$ represents a 3-chlorophenyl, 3-fluorophenyl, 3,6-difluorophenyl, 2,6-difluorophenyl, 3-methoxyphenyl, 3-trifluoromethylphenyl, 3-trifluoromethoxyphenyl, a benzyl, a 4-trifluoromethylbenzyl or a 2-trifluoromethyl-4-methylfuryl group;

$R_2$ represents a hydrogen atom;

$R_3$ represents a cyano, methoxy or dimethylaminocarbonyl group;

$R_4$ represents a 4-chlorophenyl, a 4-methoxy or a 4-propanesulphonyloxy;

$R_5$ represents a 2,4-dichlorophenyl or a 2-chlorophenyl; in the form of a base or of a salt of addition to acids as well as in the form of hydrates or of solvates.

Quite particularly, the following compounds are preferred:

—N-{[5-(4-chlorophenyl)-4-cyano-1-(2,4-dichlorophenyl)-1H-pyrazol-3-yl]methyl}-3-cyanobenzenesulfonamide,
—N-{[5-(4-chlorophenyl)-4-cyano-1-(2,4-dichlorophenyl)-1H-pyrazol-3-yl]methyl}-3-trifluorobenzenesulfonamide,
—N-{[5-(4-chlorophenyl)-4-cyano-1-(2,4-dichlorophenyl)-1H-pyrazol-3-yl]methyl}-2-trifluoromethoxybenzenesulfonamide,
—N-{[5-(4-chlorophenyl)-4-cyano-1-(2,4-dichlorophenyl)-1H-pyrazol-3-yl]methyl}-3-methoxybenzenesulfonamide,
—N-{[5-(4-chlorophenyl)-4-cyano-1-(2,4-dichlorophenyl)-1H-pyrazol-3-yl]methyl}-3-chlorobenzenesulfonamide,
—N-{[5-(4-chlorophenyl)-4-cyano-1-(2-chlorophenyl)-1H-pyrazol-3-yl]methyl}-3-fluorobenzenesulfonamide,
—N-{[5-(4-chlorophenyl)-4-cyano-1-(2-chlorophenyl)-1H-pyrazol-3-yl]methyl}-2-fluorobenzenesulfonamide,
—N-{[5-(4-chlorophenyl)-4-cyano-1-(2-chlorophenyl)-1H-pyrazol-3-yl]methyl}-2-trifluoromethoxybenzenesulfonamide,
—N-{[5-(4-methoxyphenyl)-4-cyano-1-(2,4-dichlorophenyl)-1-pyrazol-3-yl]methyl}-3,5-difluorobenzenesulfonamide,
—N-{[5-(4-propanesulphonyloxyphenyl)-4-cyano-1-(2,4-dichlorophenyl)-1H-pyrazol-3-yl]methyl}-3,5-difluorobenzenesulfonamide,
—N-{[5-(4-chlorophenyl)-4-methoxy-1-(2,4-dichlorophenyl)-1H-pyrazol-3-yl]methyl}-3-chlorobenzenesulfonamide,
-5-(4-chlorophenyl)-3-({[(3-chlorophenyl)sulfonyl]amino}methyl)-1-(2,4-dichlorophenyl)-N-methyl-1H-pyrazole-4-carboxamide,
—N-{[5-(4-chlorophenyl)-4-cyano-1-(2,4-dichlorophenyl)-1H-pyrazol-3-yl]methyl}-1-phenylmethanesulfonamide,
—N-{[5-(4-chlorophenyl)-4-cyano-1-(2,4-dichlorophenyl)-1H-pyrazol-3-yl]methyl}-5-methyl-2-(trifluoromethyl)furan-3-sulfonamide;

in the form of a base or of a salt of addition to acids as well as in the form of hydrates or of solvates.

In accordance with the invention, the compounds of formula (I) can be prepared according to a method which is characterized in that: a compound of formula:

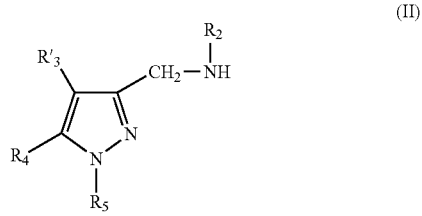

(II)

in which $R_2$, $R_4$, $R_5$ are as defined for a compound of formula (I) and $R_{13}$ represents $R_3$ or a precursor of $R_3$, is reacted, in the presence of a base and in a solvent, with a sulfonyl halide of formula $HalSO_2R_1$, in which $R_1$ is as defined for a compound of formula (I) and Hal represents a halogen atom.

If applicable, the compound obtained of formula:

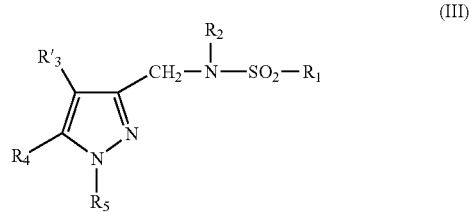

(III)

in which $R_{13}$ is $R_3$ or a precursor of $R_3$, is converted to a compound of formula (I).

Optionally, the compound of formula (I) is converted to one of its salts of addition to an acid.

The compounds of formula (I) in which $R_2$ represents a $(C_1-C_3)$alkyl can also be prepared from the corresponding compounds of formula (I) in which $R_2$ represents a hydrogen atom by a method selected from the methods known by a person skilled in the art. Among the latter we may mention alkylation by an alkyl halide, reductive amination by an aldehyde in a reducing medium, or alternatively acylation by an acyl chloride, followed by a reduction.

The compounds of formula (I) in which $R_2$ represents a $(C_1-C_4)$alkylsulfonyl group can be prepared by substitution of the compounds of formula (I) in which $R_2$ is a hydrogen atom, using methods known by a person skilled in the art.

"Precursor of $R_3$" means a group that can easily be converted to a substituent $R_3$ according to the invention.

According to the method of the present invention, the reaction of coupling of a compound of formula (II) with a sulfonyl halide is carried out in the presence of a base such as triethylamine or diisopropylethylamine, in a solvent such as dichloromethane or tetrahydrofuran, and at a temperature between room temperature and the reflux temperature of the solvent.

The compounds of formula (I) thus obtained can then be separated from the reaction mixture and purified by classical methods, for example by crystallization or chromatography.

In the case of the compounds of formula ($I_E$), the group $R'_3$, precursor of $R_3$, represents a (tetrahydropyranyloxymethyl) —$CH_2OTHP$ group.

The compound of formula:

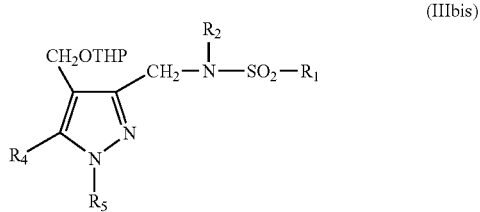

(IIIbis)

obtained by the method according to the present invention is then hydrolyzed in an acid medium to give a compound of formula ($I_E$) in which $R_3$ is a hydroxymethyl.

The compounds of formula ($I_C$; $R_3$=($C_1$-$C_4$)alkoxy) can be used for obtaining the compounds of formula ($I_B$; $R_3$=OH) by dealkylation, for example by the action of $BBr_3$ or HBr.

Using appropriate treatments, known by a person skilled in the art, the hydroxymethyl group is transformed to obtain the compounds of formula ($I_I$) to ($I_M$) in which $R_3$ has various values.

The compounds of formula ($I_K$; $R_3$=tetrazolyl) and ($I_M$; $R_3$=tetrazolylmethyl) can also be prepared from the compounds of formula ($I_A$; $R_3$=CN) and ($I_D$; $R_3$=$CH_2CN$).

The intermediates of formula (II) can be prepared in various ways depending on the value of the substituent $R_3$.

When $R_3$ represents a cyano, the following reaction scheme is adopted:

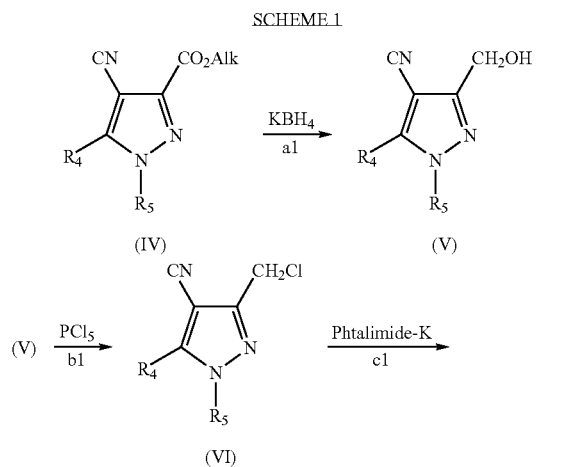

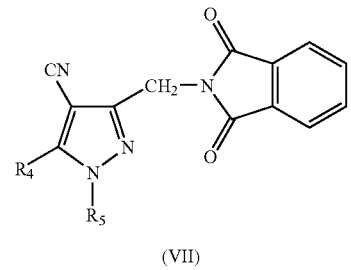

(VII)

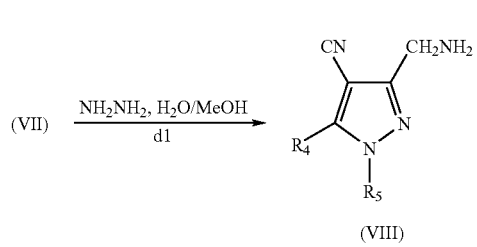

(VIII)

The compound of formula (IV) is prepared according to the method described in patent application WO 2005/000820. Selective reduction of the ester function by $KBH_4$ or $LiAlH_4$ is carried out in stage a1. The compound of formula (V) is halogenated, for example by $PCl_5$, in stage b1. The compound of formula (VI) thus obtained is then treated with potassium phthalimide, then, in stage d1, hydrazine hydrate is reacted in an alcohol to obtain the compound of formula (VIII) which corresponds to the intermediate of formula (II) in which the substituent $R_3$ is a cyano.

When $R_3$ represents a ($C_1$-$C_4$)alkoxy, the following reaction scheme is followed for preparing the corresponding intermediate of formula (II).

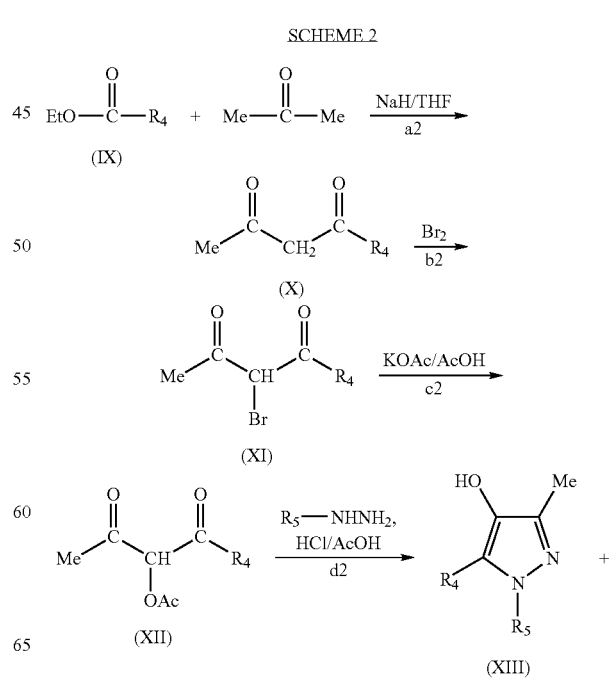

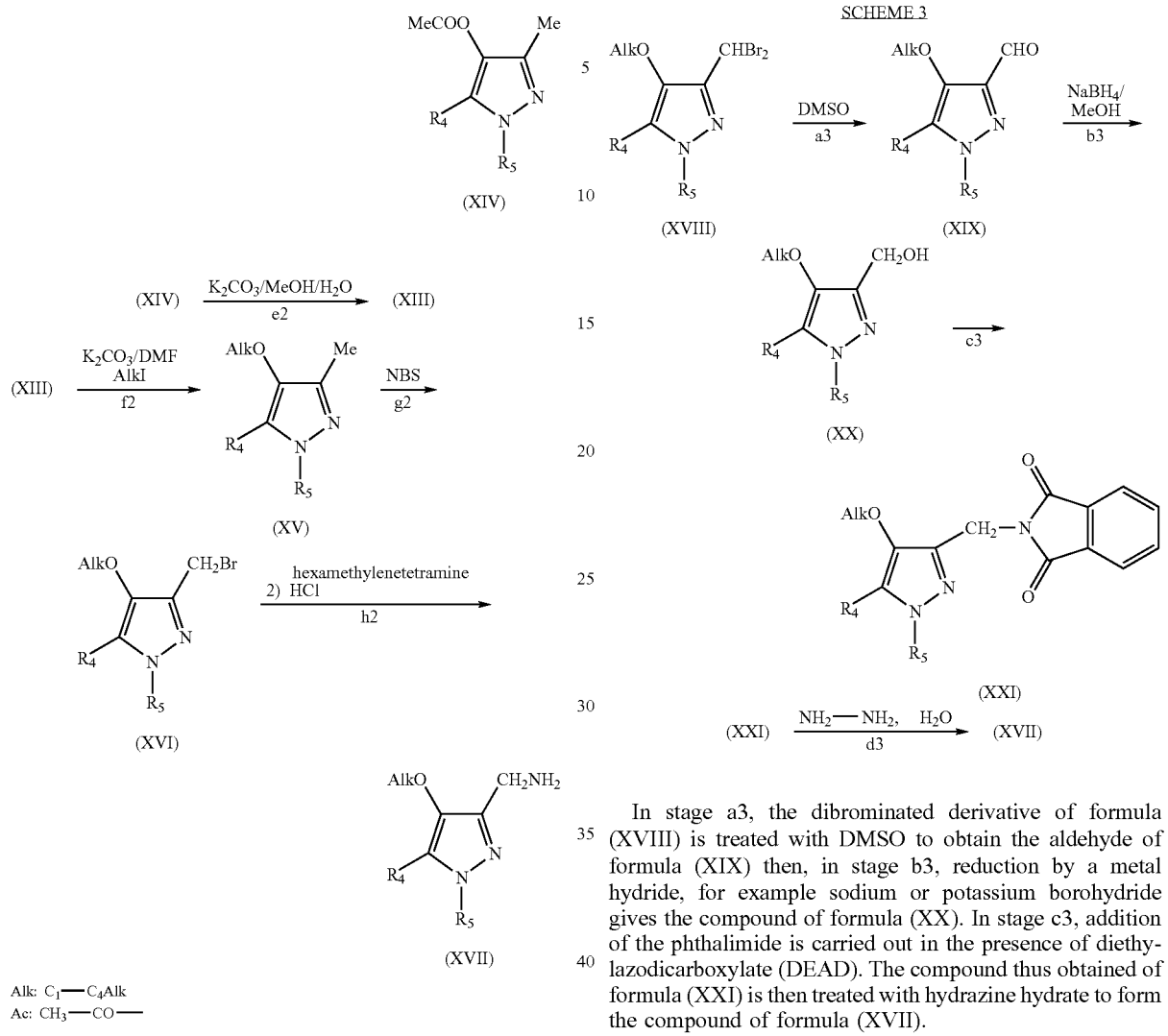

Alk: $C_1$—$C_4$Alk
Ac: $CH_3$—CO—

In stage a2, the arylbutane-1,3-dione derivative (X) is prepared by the action of acetone and of a hydride such as sodium hydride in THF on the ester $R_4CO_2Et$. The compound of formula (XI) is obtained by bromination, followed by acetylation in stage c2 to form the compound of formula (XII). In stage d2, the action of the arylhydrazine hydrochloride leads to the mixture of compounds of formula (XIII) and (XIV). The compound of formula (XIV) is hydrolyzed and is converted to a compound of formula (XIII). Then the compound of formula (XIII) is treated with a ($C_1$-$C_4$)alkyl halide of formula AlkI to form the compound of formula (XV). In stage g2, the action of N-bromosuccinimide (NBS) is used for preparing the compound of formula (XVI) then in stage h2, the action of hexamethylenetetramine is used to form the compound of formula (XVII) corresponding to the intermediate of formula (II) in which $R_3$ is a ($C_1$-$C_4$)alkoxy.

In stage g2, bromination can also lead to a dibrominated compound of formula (XVIII). Starting from this compound, a compound of formula (XVII) can be prepared in accordance with the following reaction scheme:

In stage a3, the dibrominated derivative of formula (XVIII) is treated with DMSO to obtain the aldehyde of formula (XIX) then, in stage b3, reduction by a metal hydride, for example sodium or potassium borohydride gives the compound of formula (XX). In stage c3, addition of the phthalimide is carried out in the presence of diethylazodicarboxylate (DEAD). The compound thus obtained of formula (XXI) is then treated with hydrazine hydrate to form the compound of formula (XVII).

When $R_3$ represents a cyanomethyl, ($C_1$-$C_4$)alkoxymethyl, fluoromethyl or ($C_1$-$C_4$)alkylthiomethyl group, the corresponding intermediates of formula (II) are prepared according to the reaction scheme shown below.

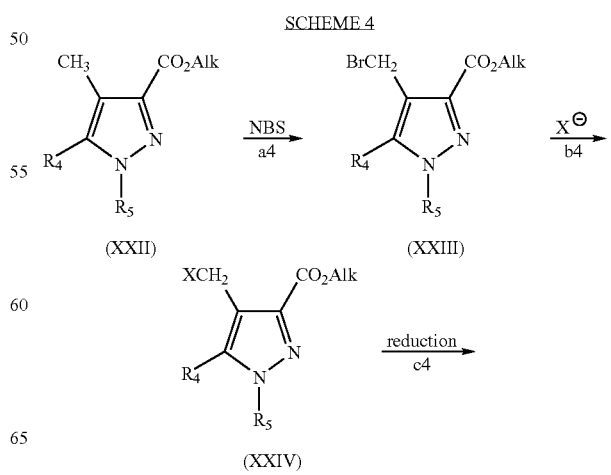

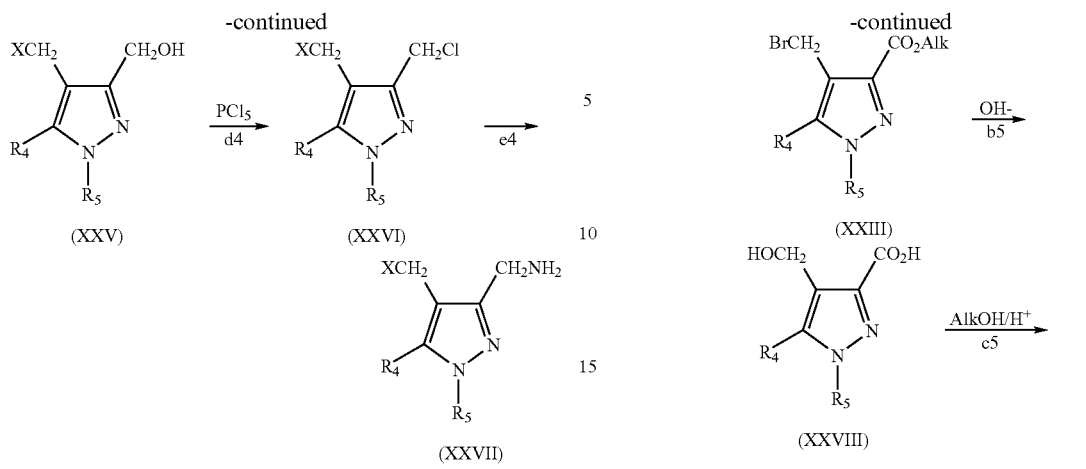

The compounds of formula (XXII) are described in patent EP 576 357.

In stage a4, the methyl group of the compound of formula (XXII) is brominated by the action of NBS.

In stage b4, the bromine is replaced with a nucleophilic group X selected from a fluorine atom, a cyano, a ($C_1$-$C_4$) alkoxy, a ($C_1$-$C_4$)alkylthio. Then the ester function is reduced with a reducing agent such as $LiAlH_4$ or $KBH_4$ to form the compound of formula (XXV). In stage d4, this compound is treated with an agent such as $PCl_5$ to give the compound of formula (XXVI). In stage e4, the successive action of potassium phthalimide and hydrazine or alternatively hexamethylene tetramine and hydrochloric acid leads to formation of the compound of formula (XXVIII) corresponding to a compound of formula (II) in which $R_2$ is $CH_2X$.

When $R_3$ represents a $CH_2SOAlk$ or $CH_2SO_2$ Alk group, the corresponding intermediates of formula (II) are prepared from the intermediate of formula (XXIV) in which X=SAlk by a reaction of oxidation to obtain the intermediates of formula (XXIV) in which X=SOAlk or $SO_2Alk$. The oxidizing agent can be metachloroperbenzoic acid or alternatively hydrogen peroxide. The intermediates of formula (XXIV) are then treated as in Scheme 4.

For preparing the intermediate of formula (II) in which $R'_3$ is a precursor of hydroxymethyl, i.e. a tetrahydropyranyloxymethyl group ($CH_2OTHP$), the following reaction scheme is followed.

SCHEME 5

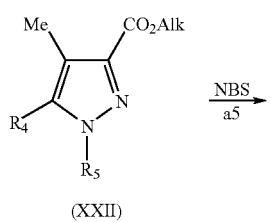

Stage a5 is carried out as described above for stage a4. In stage b5, substitution of bromine with the OH group and hydrolysis of the ester in a basic medium lead to the compound of formula (XXVIII). This compound is esterified in an acid medium to form the compound of formula (XXIX) then in stage d5, the hydroxyl group is protected with a group such as tetrahydropyranyl or tert-butoxymethyl. Then stages e5, f5 and g5 as described above for Scheme 1 are carried out for preparing the compound of formula (XXXIII) corresponding to an intermediate of formula (II) in which $R'_3$ is a tetrahydropyranyloxymethyl group.

The method according to the invention is applied to the compound of formula (XXXIII) in order to prepare a compound of formula:

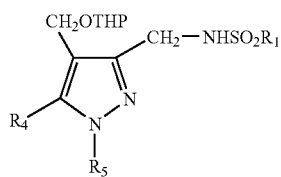
(XXXIV)

To obtain a compound according to the invention of formula (I) in which $R_3$ is a hydroxymethyl, the compound of formula (XXXIII) is treated in an acid medium, in an alcoholic solvent such as methanol.

From the compound thus obtained of formula:

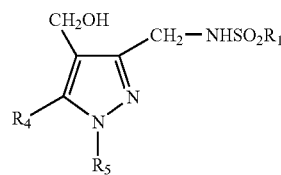
(XXXV)

a derivative of pyrazole-carboxylic acid of the following formula is prepared by oxidation:

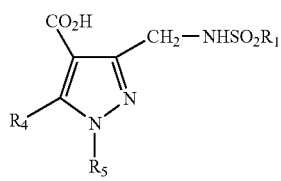
(XXXVI)

Using methods known by a person skilled in the art, we can then prepare the compounds according to the invention of formula:

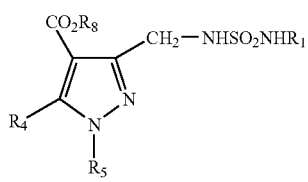
(XXXVII)

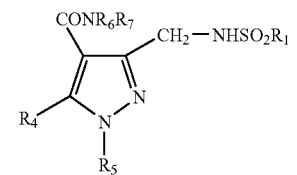
(XXXVIII)

Starting from a compound according to the invention of formula (XXXV) or (XXXX) in which $R_3$ is a hydroxymethyl or a cyanomethyl, we can prepare a compound according to the invention of formula (I) in which $R_3$ is a tetrazolylmethyl according to one of the following reaction schemes:

SCHEME 6

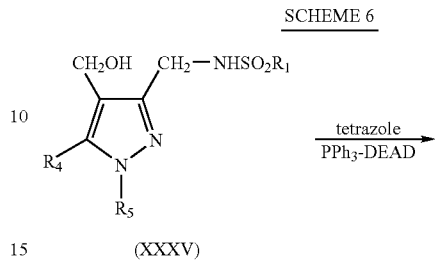
(XXXIX)

SCHEME 7

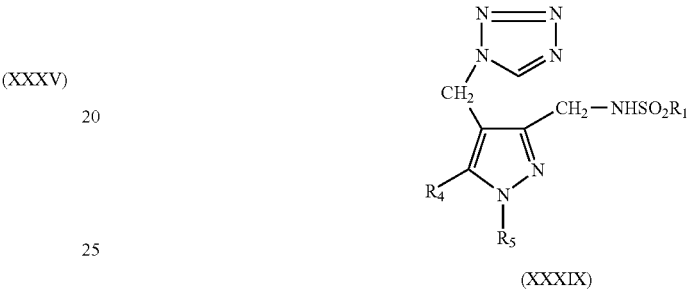

(XXXX)

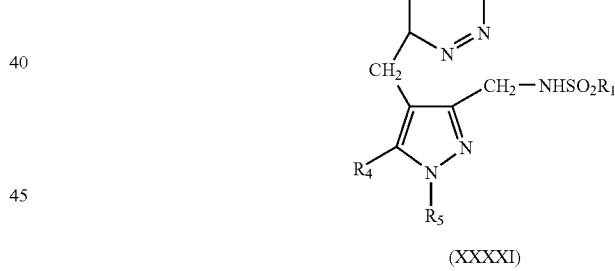
(XXXXI)

Starting from a compound according to the invention of formula (I) in which $R_3$ represents a cyano, one can prepare a compound of formula (I) in which $R_3$ represents a tetrazolyl by the action of tributyltin azide in a solvent such as xylene according to the following reaction scheme:

SCHEME 8

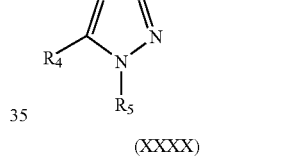
($I_A$, $R_3$ = CN)

-continued

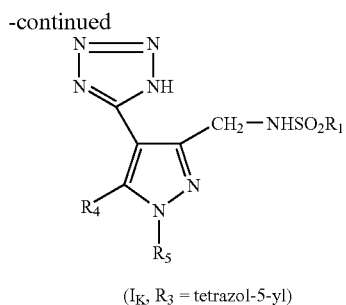

($I_K$, $R_3$ = tetrazol-5-yl)

If applicable, a compound according to the invention of formula (I) in which $R_3$ is an N-(methyl)tetrazolyl, or an N-(methyl)tetrazolylmethyl is prepared by alkylation of the tetrazole by an alkylating agent.

When $R_3$ represents a group —$CH_2NR_6R_7$, the compound of formula (II) is prepared according to the following reaction scheme:

SCHEME 9

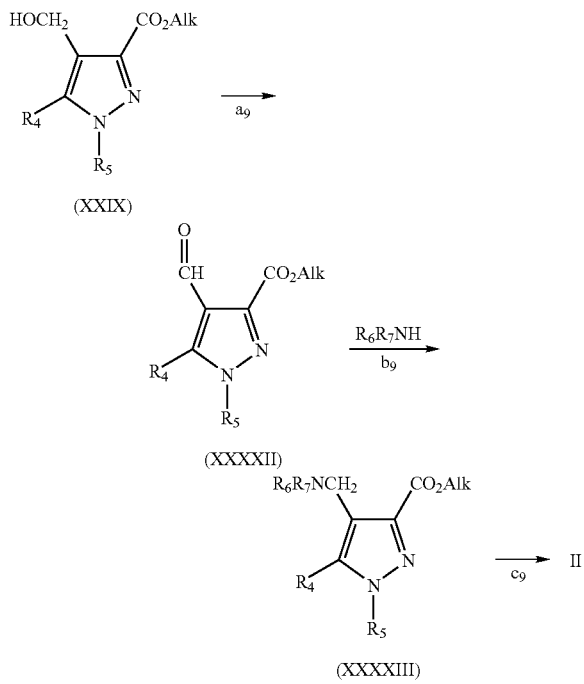

The oxidation in stage $a_9$ is carried out for example by the action of pyridinium chlorochromate according to J. Heterocycl. Chem. 1997, 34, 963.

A reductive amination is carried out in stage $b_9$.

In stage $c_9$, the compound obtained of formula (XXXXIV) is treated in accordance with stages $e_5$, $f_5$ and $g_5$ described in scheme 5 to give the compound of formula (II).

The following EXAMPLES describe the preparation of some compounds according to the invention. These examples are not limiting and are only for illustrating the present invention. The numbers of the example compounds refer to those given in TABLES 1 and 2 below, which show the chemical structures and the physical properties of some compounds according to the invention.

The following abbreviations are used in the Preparations and in the Examples:
ether: diethyl ether
iso ether: diisopropyl ether
DMSO: dimethylsulfoxide
DMF: N,N-dimethylformamide
THF: tetrahydrofuran
DCM: dichloromethane
AcOEt: ethyl acetate
MeOH: methanol
EtOH: ethanol
AcOH: acetic acid
DIPEA: diisopropylethylamine
TFA: trifluoroacetic acid
2N Hydrochloric ether: 2 normal solution of hydrochloric acid in diethyl ether
NBS: N-bromosuccinimide
AIBN: 2,2'-Azobis(2-methylpropionitrile)
$PPh_3$: triphenylphosphine
DEAD: diethylazodicarboxylate
PTSOH: paratoluene sulfonic acid
BOP: benzotriazol-1-yloxotris(dimethylamino)phosphonium hexafluorophosphate
m.p.: melting point
RT: room temperature
b.p.: boiling point
HPLC: high-performance liquid chromatography
Silica H: silica gel 60H marketed by Merck (Darmstadt)
Buffer solution pH=2: solution of 16.66 g of $KHSO_4$ and 32.32 g of $K_2SO_4$ in 1 liter of water.

The proton nuclear magnetic resonance spectra ($^1$H-NMR) are recorded at 200 MHz in DMSO-$d_6$. The chemical shifts δ are expressed in parts per million (ppm). The following abbreviations are used for interpreting the spectra: s: singlet, d: doublet, t: triplet, q: quadruplet, m: massive, mt: multiplet, bs: broad singlet, dd: doublet of doublets.

The compounds according to the invention are analyzed by the combination LC/UV/MS (liquid chromatography/UV detection/mass spectrometry). The molecular peak ($MH^+$) and the retention time (rt) in minutes are measured.

Conditions A:

Column used: Symmetry C18 of 2.1×50 mm, 3.5 µm, at 30° C., flow rate 0.4 ml/minute.

The eluent has the following composition:
solvent A: 0.005% of trifluoroacetic acid (TFA) in water at pH 3.15;
solvent B: 0.005% of TFA in acetonitrile.

| Gradient: | | |
|---|---|---|
| Time (min) | % A | % B |
| 0 | 100 | 0 |
| 10 | 10 | 90 |
| 15 | 10 | 90 |
| 16 | 100 | 0 |
| 20 | 100 | 0 |

UV detection is performed at λ=210 nm and detection of mass in positive ESI (electrospray ionization) chemical ionization mode.

Conditions MS2

Column used: XTERRA MS C18 of 2.1×30 mm, 3.5 µm, flow rate 0.8 ml/minute.

The eluent has the following composition:
Solvent A: 0.025% of TFA in water.
Solvent B: 0.025% of TFA in acetonitrile.

| Gradient | | |
| --- | --- | --- |
| Time (min) | % A | % B |
| 0 | 100 | 0 |
| 2 | 0 | 100 |
| 2.7 | 0 | 100 |
| 2.75 | 100 | 0 |

UV detection is performed with an iodine array detector between 210 and 400 nm and detection of mass in positive ESI mode.
Conditions MS5
These conditions of LC/MS analysis are similar to conditions MS2, with a flow rate of 1 ml/min.
Preparation 1

3-(Aminomethyl)-1-(2,4-dichlorophenyl)-5-(4-methoxyphenyl)-1H-pyrazole-4-carbonitrile hydrochloride A) 1-(2,4-Dichlorophenyl)-3-hydroxymethyl-5-(4-methoxyphenyl)-1H-pyrazole-4-carbonitrile A solution of 11.5 g of ethyl 4-cyano-1-(2,4-dichlorophenyl)-5-(4-methoxyphenyl)-1H-pyrazole-3-carboxylate (prepared according to patent application WO 2005/000820) in 150 ml of THF is prepared and 1.8 g of $KBH_4$ and 1.5 g of LiCl are added, then it is stirred overnight at RT and it is heated under reflux for 2.5 hours. The reaction mixture is cooled to RT then filtered and washed with THF. The filtrate is evaporated to dryness then the residue is diluted with AcOEt and washed with water. The organic phase is dried over $Na_2SO_4$, filtered and evaporated to dryness. The residue is triturated in pentane then filtered. 10 g of the expected compound is obtained.

B) 3-(Chloromethyl)-1-(2,4-dichlorophenyl)-5-(4-methoxyphenyl)-1H-pyrazole-4-carbonitrile 7.2 g of $PCl_5$ is added in small portions at 0° C. to a solution of 10 g of the compound obtained in the preceding stage in 200 ml of DCM, and it is stirred for 20 minutes at 0° C. then 24 hours at RT. The reaction mixture is poured onto water/ice mixture then the organic phase is separated and the aqueous phase is extracted again with DCM. The organic phases are combined and dried over $Na_2SO_4$ then filtered and evaporated to dryness. The residue is triturated in pentane and 9.3 g of the expected compound is obtained.

C) 1-(2,4-Dichloromethyl)-3-((1,3-dioxo-1,3-dihydro-2H-isoindol-2-yl)methyl)-5-(4-methoxy)-1H-pyrazole-4-carbonitrile 5.3 g of potassium phthalimide and 3.5 g of NaI are added to 9.3 g of the compound obtained in the preceding stage in 100 ml of DMF and it is heated at 65° C. for 2.5 hours. On returning to RT, the DMF is evaporated and then the residue is taken up in AcOEt and washed with an aqueous solution of 1N NaOH. The organic phase is dried over $Na_2SO_4$, filtered and evaporated to dryness. The residue is taken up in DCM, washed with an aqueous solution of 1N NaOH then with saturated NaCl solution. The organic phase is dried over $Na_2SO_4$, filtered and evaporated to dryness to give the expected compound. (p=10.53)

D) 3-(Aminomethyl)-1-(2,4-dichlorophenyl)-5-(4-methoxyphenyl)-1H-pyrazole-4-carbonitrile hydrochloride 10.5 g of the phthalimide derivative obtained in the preceding stage is suspended in 250 ml of ethanol, 2.1 ml of hydrazine monohydrate is added and it is heated under reflux for 1 hour. The reaction mixture is filtered and then the organic phase is evaporated to dryness. The residue is taken up in ether and a solution of HCl in hydrochloric ether is added. The precipitate that forms is filtered then rinsed with pentane. 5 g of the expected compound is obtained, m.p.=128° C.
Preparation 2

1-(5-(4-Chlorophenyl)-1-(2,4-dichlorophenyl)-4-methoxy-1H-pyrazol-3-yl) methanamine The LC/MS analyses are performed according to conditions A.

A) 1-(4-Chlorophenyl)butane-1,3-dione

A mixture containing 45 g of ethyl 4-chlorobenzoate in 235 ml of anhydrous THF and 19.50 g of NaH (60% in mineral oil) in 235 ml of anhydrous THF is placed under nitrogen. 36 ml of acetone and 750 ml of additional anhydrous THF are added dropwise at 0° C., and it is heated under reflux for 3 hours. The mixture is acidified to pH=5 by addition of 2N HCl then it is extracted with ether and washed with water and then with saturated $NaHCO_3$ solution; it is dried over $MgSO_4$ and concentrated. The raw product is dissolved in a minimum of toluene, the insoluble matter is filtered then it is purified by chromatography on silica, eluting with cyclohexane/AcOEt mixture (95/5; v/v). 47.9 g of the expected compound is obtained.
LC/MS: $MH^+$=197.0; rt=9.67 min.

B) 2-Bromo-1-(4-chlorophenyl)butane-1,3-dione 15.35 g of the compound from the preceding stage in 20 ml of DCM is placed under nitrogen and 4.04 ml of bromine is added dropwise at 0° C. At the end of addition, it is evaporated to dryness then 300 ml of DCM is added; it is washed with water, dried over $Na_2SO_4$ then filtered and evaporated to dryness. 21.15 g of the expected compound is obtained.

C) 1-(4-Chlorobenzoyl)-2-oxopropyl acetate 16.74 g of potassium acetate dissolved in 76.76 ml of hot acetic acid is placed under nitrogen. 21.5 g of the bromine derivative obtained in the preceding stage is added, in portions, at 100° C., and it is heated at 120° C. for 3 hours. The reaction mixture is poured into 1 liter of water and it is extracted with 500 ml of ether. The ether phase is washed twice with 250 ml of saturated $NaHCO_3$ solution then it is dried over Na$_2$SO$_4$, filtered and evaporated to dryness. 16.28 g of the expected compound is obtained.

LC/MS: MH$^+$=255.0; rt=8.42 min.

D) 5-(4-Chlorophenyl)-1-(2,4-dichlorophenyl)-3-methyl-1H-pyrazol-4-yl acetate A mixture containing 16.23 g of the compound from the preceding stage and 13.92 g of (2,4-dichlorophenyl)hydrazine hydrochloride is heated under reflux for 3 hours. On returning to RT, 400 ml of water is added then the organic phase is washed with saturated NaHCO$_3$ solution, then with water, and then dried over Na$_2$SO$_4$. It is filtered and evaporated to dryness. The product obtained is purified by chromatography on silica, eluting with a DCM/MeOH mixture (98/2; v/v). 5.80 g of the expected compound (LC/MS: MH$^+$=395.0; rt=10.80 min) and 4.63 g of the deacetylated compound identical to that prepared in the next stage are obtained.

E) 5-(4-Chlorophenyl)-1-(2,4-dichlorophenyl)-3-methyl-1H-pyrazol-4-ol 16.2 g of the compound obtained in the preceding stage in 82 ml of methanol is mixed with 7.1 g of potassium carbonate in solution in water (v/v) and it is stirred for 4 hours at RT. The reaction mixture is concentrated and then diluted by adding 500 ml of water and it is extracted with 500 ml of DCM. The organic phase is washed with a buffer solution at pH=2 of distilled water, then dried over Na$_2$SO$_4$, filtered and evaporated to dryness. 11.56 g of the expected compound is obtained.

LC/MS: MH$^+$ 355.0, rt=9.69 min.

F) 5-(4-Chlorophenyl)-1-(2,4-dichlorophenyl)-4-methoxy-3-methyl-1H-pyrazole 16.25 g of the compound obtained in the preceding stage dissolved in 200 ml of DMF is placed under nitrogen, 7.05 g of K$_2$CO$_3$ and 7.21 g of CH$_3$I are added, then it is heated at 60° C. under nitrogen, stifling for 3 hours. On returning to RT, the reaction mixture is filtered. 100 ml of water is added to the filtrate and it is extracted with 100 ml of DCM (twice). The organic phase is washed with 100 ml of water (5 times) then dried over Na$_2$SO$_4$, filtered and concentrated to dryness. The residue is purified on a silica column. 9.07 g of the expected compound is obtained.

LC/MS: MH$^+$=367.0; rt=11.10 min.

G) 3-Bromomethyl-5-(4-chlorophenyl)-1-(2,4-dichlorophenyl)-4-methoxy-1H-pyrazole 9.07 g of the compound obtained in the preceding stage in 125 ml of CCl$_4$ is placed under nitrogen and 4.87 g of NBS, 0.79 g of benzoyl peroxide and 0.1 g of AIBN are added, then it is heated under reflux for 60 hours. On returning to RT, it is filtered on Celite® and evaporated to dryness, then it is purified by chromatography on silica, eluting with cyclohexane/AcOEt (95/5; v/v). Besides the monobromine compound expected (2.67 g), 3,3-dibromo-5-(4-chlorophenyl)-1-(2,4-dichlorophenyl)-4-methoxy-1H-pyrazole is obtained (5 g).

LC/MS: MH$^+$=446.8; rt=11.67 min.
LC/MS: MH$^+$=524.8; rt=12.06 min.

H) 1-(5-(4-Chlorophenyl)-1-(2,4-dichlorophenyl)-4-methoxy-1H-pyrazol-3-yl)methanamine A mixture containing 2.65 g of the monobromine compound obtained in the preceding stage, 2.52 g of hexamethylene tetramine and 0.90 g of NaI in 50 ml of EtOH is placed under nitrogen. It is stirred at RT for 18 hours, then 10 ml of concentrated HCl and 12 ml of ethanol are added and it is heated under reflux for 12 hours. On returning to RT, the mixture is filtered then the filtrate is evaporated to dryness and then taken up in DCM. The organic phase is extracted with 100 ml of 10% HCl. The aqueous phase is washed with DCM then basified and extracted with DCM. The organic phase is dried over Na$_2$SO$_4$, filtered and evaporated to dryness. The residue is purified on silica, eluting with DCM/MeOH (93/7; v/v). 1.47 g of the expected compound is obtained.

LC/MS: MH$^+$=382.0; rt=6.83 min.

I) 5-(4-Chlorophenyl)-1-(2,4-dichlorophenyl)-4-methoxy-1H-pyrazole-3-carbaldehyde Under nitrogen, 5 g of the 3,3-dibromo-5-(4-chlorophenyl)-1-(2,4-dichlorophenyl)-4-methoxy-1H-pyrazole obtained in stage G is placed in 30 ml of DMSO, and it is heated at 120° C. for 6 hours. The reaction mixture is poured into 100 ml of water and it is extracted twice with 100 ml of AcOEt. The organic phase is washed with 100 ml of saturated NaCl and then dried over Na$_2$SO$_4$. After evaporating to dryness, 4 g of the unpurified expected compound is obtained.

LC/MS: MH$^+$=381.0; rt=11.06 min.

J) (5-(4-Chlorophenyl)-1-(2,4-dichlorophenyl)-4-methoxy-1H-pyrazol-3-yl)methanol 4 g of the compound obtained in the preceding stage is placed in 104 ml of methanol and 0.99 g of NaBH$_4$ is added at 0° C., and it is stilted at 0° C. for 45 minutes. 3 ml of AcOH is added to decompose excess NaBH$_4$. It is evaporated to dryness then the residue taken up in 100 ml of DCM, it is washed with 100 ml of saturated NaHCO$_3$ solution (twice) then the organic phase is dried and it is concentrated to dryness. 3.6 g of the unpurified expected compound is obtained.

LC/MS: MH$^+$=383.0; rt=9.68 min.

K) 2-((5-(4-Chlorophenyl)-1-(2,4-dichlorophenyl)-4-methoxy-1H-pyrazol-3-yl)methyl)-1H-isoindole-1,3-(2H)-dione 3.6 g of the compound obtained in the preceding stage, 2.46 g of PPh$_3$ and 1.38 g of phthalimide in solution in 156 ml of THF are mixed together. 1.63 g of DEAD is added dropwise at −10° C., and it is left overnight at RT. The reaction mixture is treated with 100 ml of a buffer solution to pH=2; the organic phase is diluted with 200 ml of ether then it is washed with 100 ml of saturated NaHCO$_3$ solution and then 100 ml of saturated NaCl solution; it is dried over Na$_2$SO$_4$, filtered and evaporated to dryness. The product obtained is purified on silica, eluting with a DCM/MeOH mixture (98/2; v/v). 3.4 g of the expected compound is obtained.

LC/MS: MH$^+$=512.0; rt=11.43 min.

L) 1-(5-(4-Chlorophenyl)-1-(2,4-dichlorophenyl)-4-methoxy-1H-pyrazol-3-yl) methanamine 3.4 g of the compound obtained in the preceding stage and 0.67 g of hydrazine monohydrate in solution in 95 ml of methanol are placed under nitrogen, and heated under reflux for 3 hours. The reaction mixture is evaporated to dryness, the residue is taken up in 150 ml of ether; the organic phase is washed with 10% NaOH solution then with saturated NaHCO$_3$ solution and then with saturated NaCl solution. It is extracted with DCM and then evaporated to dryness. 2.45 g of the expected compound, identical to that obtained in stage H, is obtained.

Preparation 3

1-(5-(4-Chlorophenyl)-1-(2,4-dichlorophenyl)-4-(tetrahydro-2H-pyran-2-yloxymethyl)-1H-pyrazol-3-yl)methanamine

A) Methyl 4-(bromomethyl)-5-(4-chlorophenyl)-1-(2,4-dichlorophenyl)-1H-pyrazole-3-carboxylate 19 g of methyl 5-(4-chlorophenyl)-1-(2,4-dichlorophenyl)-4-methyl-1H-pyrazole-3-carboxylate is placed in 200 ml of CCl$_4$ and 8.54 g of NBS and then 1 g of benzoyl peroxide are added, heating under reflux overnight. On returning to RT, the precipitate that forms is filtered and washed with CCl$_4$. All of the filtrate is evaporated, then taken up in AcOEt and washed with saturated NaCl solution (twice). It is dried over MgSO$_4$ and evaporated. The expected compound crystallizes in iso ether, it is filtered and dried to obtain 19.4 g of the expected compound.

B) 5-(4-Chlorophenyl)-1-(2,4-dichlorophenyl)-4-hydroxymethyl-1H-pyrazole-3-carboxylic acid 17 g of the compound obtained in the preceding stage and 1.5 g of LiOH, H$_2$O are placed in 100 ml of THF and 50 ml of water and heated for 3 hours and then stirred overnight at RT. The precipitate that forms is filtered and then the filtrate is evaporated. The residue is taken up in AcOEt then washed with saturated NaCl solution. It is dried over MgSO$_4$, filtered, and the filtrate is concentrated to obtain 11 g of the expected compound.

C) Methyl 5-(4-chlorophenyl)-1-(2,4-dichlorophenyl)-4-hydroxymethyl-1H-pyrazole-3-carboxylate 10 g of the acid formed in the preceding stage is dissolved in 100 ml of MeOH, 1 ml of concentrated H$_2$SO$_4$ is added and heated under reflux for 2 hours. After cooling, and evaporating the solvent, it is taken up in AcOEt. It is washed with NaHCO$_3$ solution then with saturated NaCl solution and it is dried over MgSO$_4$. It is purified by chromatography, eluting with AcOEt/cyclohexane mixture (10/90 then 20/80; v/v). 2.8 g of the expected compound which crystallizes with iso ether is obtained.

D) Methyl 5-(4-Chlorophenyl)-1-(2,4-dichlorophenyl)-4-(tetrahydro-2H-pyran-2-yloxymethyl)-1H-pyrazole-3-carboxylate 2.8 g of the compound obtained in the preceding stage is dissolved in 48 ml of DCM, 0.68 g of 3,4-dihydro-2H-pyrane and 0.07 g of PTSOH are added, then it is stirred at RT for 1 hour. The reaction mixture is washed with a solution of NaHCO$_3$ then with saturated NaCl solution. It is dried over MgSO$_4$ and evaporated. The product obtained is purified by chromatography on silica, eluting with AcOEt/cyclohexane mixture (5/95 then 90/10; v/v). The expected compound crystallizes in cyclohexane/AcOEt. 2.2 g is obtained.

E) 2-(5-(4-Chlorophenyl)-1-(2,4-dichlorophenyl)-4-(tetrahydro-2H-pyran-2-yloxymethyl)-1H-pyrazol-3-yl)methyl)-1,3-bis(methylene)isoindoline 2.6 g of the compound obtained in the preceding stage, 0.97 g of phthalimide then 1.74 g of PPh$_3$ are dissolved in 50.5 ml of THF and 1.16 g of DEAD is added dropwise at −10° C. It is allowed to return to RT then it is stirred at RT for 96 hours. It is extracted with ether and washed with saturated NaCl solution, then it is dried over MgSO$_4$ and evaporated. The product obtained is purified by chromatography on silica, eluting with AcOEt/cyclohexane (5/95; v/v). 2.2 g of the expected compound is obtained.

F) 1-(5-(4-Chlorophenyl)-1-(2,4-dichlorophenyl)-4-(tetrahydro-2H-pyran-2-yloxymethyl)-1H-pyrazol-3-yl)methanamine 2.2 g of the compound obtained in the preceding stage is placed in 40 ml of MeOH, 0.40 ml of hydrazine hydrate is added and it is heated under reflux for 1.5 h. It is left to cool, the solvent is evaporated and it is taken up in DCM. It is washed with 10% NaOH solution then with saturated NaCl solution, it is dried over MgSO$_4$ and evaporated. 1.57 g of the expected compound in the raw form is obtained.

Preparation 4

1-(5-(4-Chlorophenyl)-1-(2,4-dichlorophenyl)-4-(methoxymethyl)-1H-pyrazol-3-yl)methanamine

A) Methyl 5-(4-Chlorophenyl)-1-(2,4-dichlorophenyl)-4-methyl-1H-pyrazole-3-carboxylate 20 g of 1-(5-(4-chlorophenyl)-1-(2,4-dichlorophenyl)-4-methyl)-1H-pyrazole-3-carboxylic acid is placed in 200 ml of MeOH, 0.5 g of toluene sulphonyl chloride is added and it is heated under reflux overnight. It is evaporated to half, then the precipitate that forms is filtered. It is washed with ether and then dried, obtaining 20.6 g of the expected compound.

B) Methyl 4-(Bromophenyl)-5-(4-chlorophenyl)-1-(2,4-dichlorophenyl)-4-(bromomethyl)-1H-pyrazole-3-carboxylate 16.5 g of the compound obtained in the preceding stage is placed in 200 ml of CCl$_4$, 7.42 g of NBS and 0.1 g of benzoyl peroxide are added then it is heated under reflux overnight. The precipitate that forms is filtered and washed with CCl$_4$. After evaporating the solvent it is taken up in DCM, then the organic phase is washed with water and then with saturated NaCl solution. It is dried over MgSO$_4$ and evaporated. The expected compound is crystallized with DCM and iso ether. 1.3 g of the expected compound is obtained.

C) Methyl 5-(4-Chlorophenyl)-1-(2,4-dichlorophenyl)-4-(methoxyphenyl)-1H-pyrazole-3-carboxylate 2.5 g of sodium is washed with 100 ml of toluene and then 100 ml of ether, then it is cut into small pieces and placed in 500 ml of MeOH. 13 g of the bromine derivative obtained in the preceding stage is added to the solution of sodium methylate thus prepared and it is stirred for 30 minutes, leaving the reaction mixture at RT for 72 hours. The precipitate that forms is filtered then the filtrate is evaporated. It is treated with 25% HCl, and taken up in AcOEt. After decanting, the organic phase is washed with saturated NaCl solution (twice). It is dried over $Na_2SO_4$ and concentrated. The expected product crystallizes in iso ether. 1 g of the expected compound is obtained.

D) 5-(4-Chlorophenyl)-1-(2,4-dichlorophenyl)-4-methoxyphenyl-1H-pyrazol-3-yl)methanol 5.8 g of the compound obtained in the preceding stage is dissolved in 100 ml of THF and 0.82 g of $LiAlH_4$ is added in small portions at 0° C. It is stirred at RT for 30 minutes and then hydrolyzed by adding 15 ml of 1N NaOH solution. The precipitate that forms is filtered then washed with THF and the filtrate is evaporated. It is taken up in AcOEt and washed with saturated NaCl solution. It is dried over $MgSO_4$ and evaporated. It is crystallized in AcOEt/iso ether. 4.6 g of the expected compound is obtained.

E) 3-(Chloromethyl)-5-(4-chlorophenyl)-1-(2,4-dichlorophenyl)-4-methoxymethyl-1H-pyrazole 4.5 g of the compound obtained in the preceding stage is dissolved in 50 ml of DCM, then 2.6 g of $PCl_5$ is added in small portions at 0° C. and it is stirred at RT for 1 hour. 25 ml of water is added and it is left overnight at RT. After decanting, the organic phase is washed with saturated NaCl solution (twice), then it is dried over $Na_2SO_4$ and evaporated. It is chromatographed on silica, eluting with AcOEt/cyclohexane mixture (10/90; v/v). 2.17 g of the expected compound and 2 g of the equivalent compound bearing the dichloromethyl substituent in position 3 are obtained.

F) 1-(5-(4-Chlorophenyl)-1-(2,4-dichlorophenyl)-4-(methoxymethyl)-1H-pyrazol-3-yl)methanamine 2 g of the compound obtained in the preceding stage is dissolved in 50 ml of chloroform and 0.80 g of hexamethylenetetramine is added, then it is stirred for several days at RT. It is evaporated to half, and 50 ml of ether is added. The precipitate that forms is filtered then it is taken up in 100 ml of EtOH and 15 ml of concentrated KCl. It is heated under reflux for 2 hours and then left overnight at RT. The precipitate of $NH_4Cl$ that forms is filtered. The filtrate is evaporated, it is taken up in DCM then washed with a solution of $NaHCO_3$ and then with saturated NaCl solution (twice). It is dried over $MgSO_4$ and evaporated. It is taken up in iso ether. It is evaporated again, obtaining 1.7 g of the expected compound.

NMR: 7.1: d: 2H, 7.45: d: 2H, 7.55: dd: 1H, 7.6: d: 1H, 7.75: d: 1H.

EXAMPLE 1

Compound No. 52

3-Chloro-N-((5-(4-chlorophenyl)-1-(2,4-dichlorophenyl)-4-methoxy-1H-pyrazol-3-yl)methyl)benzenesulfonamide 0.32 g of the compound obtained in Preparation 2 is mixed with 0.09 g of triethylamine and 0.19 g of 3-chlorobenzenesulfonyl in 20 ml of dichloromethane and is stirred for one hour at RT. It is diluted with 100 ml of DCM then washed with 10% HCl solution, then with 25% NaOH solution, then with saturated NaCl solution and it is extracted with DCM. It is dried, filtered and evaporated to dryness. The residue is purified by chromatography on silica, eluting with DCM/MeOH mixture (96/4; v/v). 0.21 g of the expected compound is obtained.

EXAMPLE 2

Compound No. 53

3-Chloro-N-((5-(4-chlorophenyl)-1-(2,4-dichlorophenyl)-4-hydroxymethyl-1H-pyrazol-3-yl)methyl)benzenesulfonamide A) 3-Chloro-N-((5-(4-chlorophenyl)-1-((tetrahydro-2H-pyran-2-yloxy)methyl)-1H-pyrazol-3-yl)methyl)benzenesulfonamide Starting from 0.7 g of the compound obtained in Preparation 3, 0.35 g of 3-chlorobenzenesulfonyl and 0.33 g of triethylamine, 0.847 g of the expected compound is obtained by following the procedure described in the preceding example.

B) 3-Chloro-N-((5-(4-chlorophenyl)-4-(hydroxymethyl)-1H-pyrazol-3-yl)methyl)benzenesulfonamide 0.847 g of the compound obtained in the preceding stage is dissolved in 40 ml of MeOH. 1 ml of concentrated HCl is added and it is heated under reflux for 10 minutes. It is left to cool, then the solvent is evaporated and the residue is taken up in AcOEt. It is washed with saturated NaCl solution (twice), then dried over $MgSO_4$ and evaporated. The product obtained is purified by chromatography, eluting with AcOEt/cyclohexane mixture (10/90 then 20/80 then 25/75; v/v). 176 mg of the expected compound and 289 mg of the corresponding compound of formula (I) in which $R_3$ is a methoxymethyl group are obtained.

EXAMPLE 3

Compound No. 48

3-Chloro-N-((5-(4-Chlorophenyl)-1-(2,4-dichlorophenyl)-4-(methoxymethyl)-1H-pyrazol-3-yl)-methyl)benzenesulfonamide 0.45 g of amine obtained in Preparation 4 is placed in 20 ml of DCM. 0.26 g of 3-chlorobenzenesulfonyl and 0.25 g of triethylamine are added, then it is stirred for 3 hours at RT. 15 ml of water is added, and it is stirred for 10 minutes. After decanting, the organic phase is washed with $NaHCO_3$/$KHSO_4$ solution then with saturated NaCl solution (twice).

It is dried over MgSO$_4$ and evaporated. It is taken up in iso ether and is then purified by chromatography on silica, eluting with AcOEt/cyclohexane (5/95; v/v). 0.23 g of the expected compound is obtained, m.p.=154° C.

EXAMPLE 4

Compound No. 55

5-(4-Chlorophenyl)-3-((((3-chlorophenyl)sulfonyl)amino)methyl)-1-(2,4-dichlorophenyl)-N,N-dimethyl-1H-pyrazole-4-carboxamide A) 5-(4-chlorophenyl)-3-((((3-chlorophenyl)sulfonyl)amino)methyl)-1-(2,4-dichlorophenyl)-1H-pyrazole-4-carboxylic acid 13.36 g of Cr$_2$O$_3$ is added to a mixture of 11.5 ml of concentrated H$_2$SO$_4$ solution, diluted in 50 ml of cold water to prepare the Jones reagent. 0.5 g of the compound from Example 2 is dissolved in 15 ml of acetone then 5 ml of the Jones reagent is added slowly at a temperature between 0° C. and 5° C. It is stirred for 2 days. 10 ml of isopropanol is added to destroy the excess reagent, and the precipitate that forms is filtered. The filtrate is extracted with 30 ml of ether. The organic phase is washed with saturated NaCl solution (twice), and then dried over MgSO$_4$. It is evaporated and taken up in hot iso ether. The expected compound crystallizes. 440 mg is obtained, m.p.=211° C.

B) 5-(4-Chlorophenyl)-3-((((3-chlorophenyl)sulfonyl)amino)methyl)-1-(2,4-dichlorophenyl)-N,N-dimethyl-1H-pyrazole-4-carboxamide 0.4 g of acid obtained in the preceding stage is dissolved in 20 ml of DCM, 0.37 g of BOP and 0.05 g of methylamine are added and it is stirred overnight at RT. 10 ml of water is added, then the organic phase is decanted. After evaporating, the residue is taken up in AcOEt. It is washed successively with solutions of K$_2$SO$_4$, NaHCO$_3$ and NaCl (saturated solution), it is dried over MgSO$_4$ and evaporated to dryness. The residue is taken up in hot Et$_2$O, then crystallized. 0.35 g of the expected compound is obtained, m.p.=178° C.

EXAMPLE 5

Compound No. 57

0.69 g of the compound from Example 1 is placed in 15 ml of DCM, 12.36 mg of BBr$_3$ is added at −20° C. then it is stirred for 1 hour at −20° C. then 3 hours at RT. 100 ml of water and 100 ml of DCM are added to the reaction mixture, it is decanted, then the organic phase is washed with 100 ml of dilute HCl; it is dried over MgSO$_4$ and evaporated to dryness. The residue is taken up in 100 ml of DCM. The expected compound precipitates, and 373 mg of the expected product is obtained.
LC/MS: MH$^+$=541.8; rt=10.69 min.

EXAMPLE 6

The compounds of formula (I$_A$) described in Table 1 are prepared either according to the methods described above, or by combinatorial chemistry according to the method described below.
The pyrazole-methylamine derivative of formula (II) is dissolved in DMF at a concentration of 0.1M in the presence of 3 equivalents of DIPEA. 300 μl of this solution is placed in each 2-ml well, and 120 μl of solution of sulfonyl chloride (R$_1$SO$_2$Cl) at a concentration of 0.25M in THF is added. The plates are agitated at RT for 16 hours, then evaporated. The products that form are dissolved in each well with 500 μl of AcOEt, 400 μl of 0.1M Na$_2$CO$_3$ is added and the plates are agitated. After decanting, 350 μl of aqueous phase is removed then 40 μl of DMF and then 300 μl of CH$_3$CN are added.

EXAMPLE 7

Compound No. 45

N-((4-cyano-1-(2,4-dichlorophenyl)-5-(4-methoxyphenyl)-1H-pyrazol-3-yl)methyl)-2,6-difluorobenzenesulfonamide 0.98 ml of triethylamine and 0.75 g of 2,6-difluorobenzenesulfonyl chloride in solution in DCM are added to a solution containing 1.2 g of the compound from Preparation 1. After stifling overnight at RT, the DCM is concentrated, the residue is taken up in AcOEt, the organic phase is washed with buffer solution pH2, then with saturated NaHCO$_3$ solution and then with saturated NaCl solution; it is dried over MgSO$_4$ and concentrated to dryness under vacuum. It is purified by chromatography on silica, eluting with cyclohexane/AcOEt mixture (90/10; v/v). 1.5 g of the expected compound is obtained. m.p.=170° C.

EXAMPLE 8

Compound No. 72

N-((4-cyano-1-(2,4-dichlorophenyl)-5-(4-hydroxyphenyl)-1H-pyrazol-3-yl)methyl)-2,6-difluorobenzenesulfonamide 1 g of the compound obtained in the preceding example is placed in 15 ml of DCM. 4.56 g of BBr$_3$ in 1M solution in DCM is introduced dropwise at −20° C., under nitrogen, it is stirred for 1 hour at −20° C., then the temperature is allowed to rise. After 72 hours at RT, the reaction mixture is poured into a water/ice/DCM mixture; the organic phase is washed with 30 ml of saturated NaHCO$_3$ solution, 30 ml of buffer solution pH2, then 2×30 ml of saturated NaCl solution. It is decanted and dried under vacuum, obtaining 0.782 g of the expected compound. m.p.=196° C.

EXAMPLE 9

Compound No. 73

N-((4-cyano)-1-(2,4-dichlorophenyl)-5-(4-((propylsulfonyl)oxy)phenyl)-1H-pyrazol-3-yl)methyl)-2,6-difluorobenzenesulfonamide A solution is prepared containing 0.35 g of the compound from the preceding example in 20 ml of DCM, and 1.44 ml of NEt$_3$ and then 0.103 g of n-propanesulfonyl chloride are added. After stirring for 1.5 h at RT, 10 ml of water is added, then it is decanted and the organic phase is washed with 15 ml of saturated NaCl solution. After removing the solvents, it is purified by chromatography on silica, eluting with cyclohexane/AcOEt mixture (90/10 to 70/30; v/v). 0.144 mg of the expected compound is obtained. m.p.=77° C.

The following tables show the chemical structures and physical properties of some compounds according to the invention.
In these tables, Me and tBu represent the methyl and tert-butyl groups, respectively.

TABLE 1

[Structure (IA): 1,5-diaryl pyrazole with 4-CN and 3-CH₂-NH-SO₂-R₁ substituents; aryl groups bear r₄/r'₄ and r₅/r'₅ substituents]

(IA)

| Compounds | r₄, r'₄ | r₅, r'₅ | R₁ | Characterization Conditions m.p. °C. |
|---|---|---|---|---|
| 1 | 4-Cl | 2,4-diCl | 2-fluorophenyl | MH⁺ = 534.8; rt = 2.00; MS5 |
| 2 | 4-Cl | 2,4-diCl | 2,6-difluorophenyl | MH⁺ = 552.7; rt = 2.04; MS5 |
| 3 | 4-Cl | 2,4-diCl | 2-thienyl | MH⁺ = 522.7; rt = 2.01; MS5; m.p. = 184 |
| 4 | 4-Cl | 2,4-diCl | 3,5-dimethylphenyl | MH⁺ = 544.8; rt = 2.13; MS5 |
| 5 | 4-Cl | 2,4-diCl | 3,5-difluorophenyl | MH⁺ = 552.7; rt = 2.08; MS5 |
| 6 | 4-Cl | 2,4-diCl | 3-cyanophenyl | MH⁺ = 541.8; rt = 2.03; MS5; m.p. = 167 |
| 7 | 4-Cl | 2,4-diCl | 4-cyanophenyl | MH⁺ = 541.8; rt = 1.99; MS5; m.p. = 187 |
| 8 | 4-Cl | 2,4-diCl | 3-(trifluoromethoxy)phenyl | MH⁺ = 600.7; rt = 2.12; MS5; m.p. = 126 |

TABLE 1-continued (IA)

| Compounds | r₄, r'₄ | r₅, r'₅ | R₁ | Characterization Conditions m.p. ° C. |
|---|---|---|---|---|
| 9 | 4-Cl | 2,4-diCl | 4-F-phenyl | MH⁺ = 534.8 rt = 2.03 MS5 |
| 10 | 4-Cl | 2,4-diCl | 3-F-phenyl | MH⁺ = 534.8 rt = 2.07 MS5 |
| 11 | 4-Cl | 2,4-diCl | 3-CF₃-phenyl | MH⁺ = 584.7 rt = 2.09 MS5 m.p. = 104 |
| 12 | 4-Cl | 2,4-diCl | 3-OMe-phenyl | MH⁺ = 546.8 rt = 2.07 MS5 m.p. = 141 |
| 13 | 4-Cl | 2,4-diCl | 5-Me-2-CF₃-furan-3-yl | MH⁺ = 588.7 rt = 2.14 MS5 m.p. = 184 |
| 14 | 4-Cl | 2,4-diCl | —CH₂—(4-CF₃-phenyl) | MH⁺ = 598.8 rt = 2.11 MS5 m.p. = 152 |
| 15 | 4-Cl | 2,4-diCl | —CH₂—(3-CF₃-phenyl) | MH⁺ = 598.8 rt = 2.13 MS5 m.p. = 89 |
| 16 | 4-Cl | 2,4-diCl | 2,5-diCl-phenyl | MH⁺ = 584.7 rt = 2.13 MS5 m.p. = 165 |

TABLE 1-continued

[Structure (IA): pyrazole with NC and CH₂—NH—SO₂—R₁ substituents, bearing two phenyl groups with r₄,r'₄ and r₅,r'₅ substituents]

(IA)

| Compounds | r₄, r'₄ | r₅, r'₅ | R₁ | Characterization Conditions m.p. ° C. |
|---|---|---|---|---|
| 17 | 4-Cl | 2,4-diCl | —CH₂—phenyl | MH⁺ = 530.8; rt = 2.08; MS5; m.p. = 93 |
| 18 | 4-Cl | 2,4-diCl | 5-chlorothien-2-yl | MH⁺ = 556.7; rt = 2.13; MS5 |
| 19 | 4-Cl | 2,4-diCl | 3-chlorophenyl | MH⁺ = 550.7; rt = 2.11; MS5; m.p. = 98 |
| 20 | 4-Cl | 2,4-diCl | 3-chloro-4-fluorophenyl | MH⁺ = 568.7; rt = 2.10; MS5 |
| 21 | 4-Cl | 2,4-diCl | 2-(trifluoromethyl)phenyl | MH⁺ = 584.7; rt = 2.10; MS5 |
| 22 | 4-Cl | 2-Cl | 3-methoxyphenyl | MH⁺ = 513.5; rt = 1.82; MS5 |
| 23 | 4-Cl | 2-Cl | 3-fluorophenyl | MH⁺ = 501.5; rt = 1.83; MS2; m.p. = 85 |
| 24 | 4-Cl | 2-Cl | —CH₂—phenyl | MH⁺ = 497.5; rt = 1.83; MS2 |

TABLE 1-continued
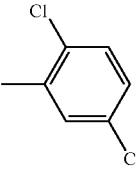
(IA)
| Compounds | r₄, r'₄ | r₅, r'₅ | R₁ | Characterization Conditions m.p. ° C. |
|---|---|---|---|---|
| 25 | 4-Cl | 2-Cl | 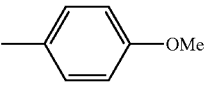 | MH⁺ = 551.4<br>rt = 1.90<br>MS2<br>m.p. = 110 |
| 26 | 4-Cl | 2-Cl | 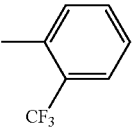 | MH⁺ = 513.5<br>rt = 1.80<br>MS2 |
| 27 | 4-Cl | 2-Cl |  | MH⁺ = 551.5<br>rt = 1.86<br>MS2 |
| 28 | 4-Cl | 2-Cl | 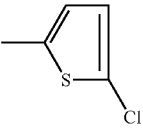 | MH⁺ = 517.4<br>rt = 1.87<br>MS2 |
| 29 | 4-Cl | 2-Cl | 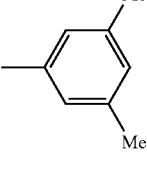 | MH⁺ = 523.4<br>rt = 1.87<br>MS2<br>m.p. = 118 |
| 30 | 4-Cl | 2-Cl | 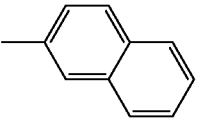 | MH⁺ = 511.5<br>rt = 1.89<br>MS2<br>m.p. = 154 |
| 31 | 4-Cl | 2-Cl | 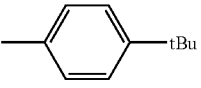 | MH⁺ = 533.5<br>rt = 1.88<br>MS2 |
| 32 | 4-Cl | 2-Cl |  | MH⁺ = 539.5<br>rt = 1.96<br>MS2 |

TABLE 1-continued (IA)

| Compounds | r₄, r'₄ | r₅, r'₅ | R₁ | Characterization Conditions m.p. ° C. |
|---|---|---|---|---|
| 33 | 4-Cl | 2-Cl | 2-fluorophenyl (with methyl) | MH⁺ = 501.5<br>rt = 1.81<br>MS2<br>m.p. = 75 |
| 34 | 4-Cl | 2-Cl | 4-methylphenyl (with methyl) | MH⁺ = 497.5<br>rt = 1.84<br>MS2 |
| 35 | 4-Cl | 2-Cl | 4-fluorophenyl (with methyl) | MH⁺ = 501.5<br>rt = 1.82<br>MS2 |
| 36 | 4-Cl | 2-Cl | 2-OCF₃-phenyl (with methyl) | MH⁺ = 567.5<br>rt = 1.88<br>MS2<br>m.p. = 87 |
| 37 | 4-Cl | 2-Cl | 3-Cl-4-Me-phenyl (with methyl) | MH⁺ = 531.5<br>rt = 1.90<br>MS2 |
| 38 | 4-Cl | 2-Cl | 3,6-dimethoxy-pyridyl (with methyl) | MH⁺ = 543.5<br>rt = 1.81<br>MS2 |
| 39 | 4-Cl | 2-Cl | 3,4,5-trimethylisoxazolyl | MH⁺ = 502.5<br>rt = 1.80<br>MS2 |
| 40 | 4-Cl | 2-Cl | 2,3-dihydrobenzofuranyl (with methyl) | MH⁺ = 525.5<br>rt = 1.81<br>MS2 |

TABLE 1-continued (IA)

| Compounds | r₄, r'₄ | r₅, r'₅ | R₁ | Characterization Conditions m.p. ° C. |
|---|---|---|---|---|
| 41 | 4-Cl | 2-Cl | 5-methylthiophen-2-yl | MH⁺ = 489.4<br>rt = 1.80<br>MS2 |
| 42 | 4-Cl | 2-Cl | 5-(dimethylamino)naphthalen-1-yl | MH⁺ = 576.5<br>rt = 1.84<br>MS2 |
| 43 | 4-Cl | 2-Cl | 3-acetylphenyl | MH⁺ = 525.5<br>rt = 1.78<br>MS5<br>m.p. = 117 |
| 44 | 4-OMe | 2,4-diCl | 3,5-difluorophenyl | MH⁺ = 548.8<br>rt = 6.67<br>MS5<br>m.p. = 153 |
| 45 | 4-OMe | 2,4-diCl | 2,6-difluorophenyl | MH⁺ = 548.8<br>rt = 6.39<br>MS5<br>m.p. = 170 |
| 46 | 4-OMe | 2,4-diCl | 3-cyanophenyl | MH⁺ = 537.8<br>rt = 6.35<br>MS5 |
| 47 | 4-OMe | 2,4-diCl | 2-(trifluoromethyl)phenyl | MH⁺ = 580.8<br>rt = 6.80<br>MS5 |

TABLE 2
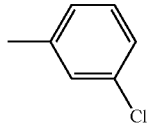
| Compounds | R₁ | R₃ | Characterization Conditions m.p. ° C. |
|---|---|---|---|
| 48 | 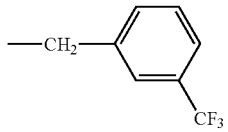 | —CH₂OMe | m.p. = 154° C. |
| 49 | 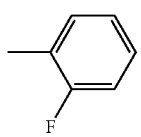 | —CH₂OMe | m.p. = 74° C. |
| 50 | 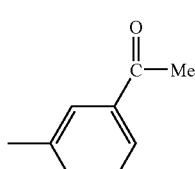 | —CH₂OMe | m.p. = 143° C. |
| 51 | 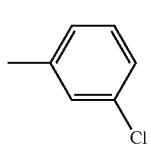 | —CH₂OMe | m.p. = 85° C. |
| 52 | 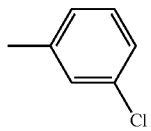 | —OMe | MH⁺ = 556.0<br>rt = 11.48 |
| 53 | 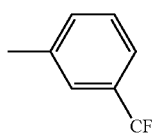 | —CH₂OH | m.p. = 83° C. |
| 54 | 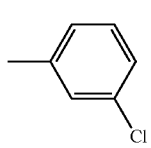 | —CH₂OH | m.p. = 82° C. |
| 55 | | | m.p. = 178° C. |

TABLE 2-continued

[Structure: 1-(2,4-dichlorophenyl)-5-(4-chlorophenyl)-pyrazole with CH₂-NH-SO₂-R₁ at position 3 and R₃ at position 4]

| Compounds | R₁ | R₃ | Characterization Conditions m.p. ° C. |
|---|---|---|---|
| 56 | 3-chlorophenyl | —C(=O)—NMe₂ | m.p. = 164° C. |
| 57 | 3-chlorophenyl | —OH | MH⁺ = 541.8 rt = 10.69 |
| 58 | 3-chlorophenyl | —C(=O)—OMe | m.p. = 132° C. |
| 59 | 3-chlorophenyl | —CH₂OEt | m.p. = 143° C. |
| 60 | —CH₂-(3-trifluoromethylphenyl) | —C(=O)—NHMe | m.p. = 98° C. |
| 61 | —CH₂-(3-trifluoromethylphenyl) | —C(=O)—NMe₂ | m.p. = 83° C. |
| 62 | —CH₂-(3-trifluoromethylphenyl) | —C(=O)—OMe | m.p. = 125° C. |
| 63 | 3-chlorophenyl | —CH₂CN | |

TABLE 2-continued

[Structure: pyrazole core with R3-CH2-NH-SO2-R1 substituent at position 3, 4-chlorophenyl at position 5, and 2,4-dichlorophenyl at position 1]

| Compounds | R₁ | R₃ | Characterization Conditions m.p. °C |
|---|---|---|---|
| 64 | 3-chlorophenyl | —CH₂—(tetrazol-5-yl) | |
| 65 | 3-chlorophenyl | —CH₂—(tetrazol-5-yl) | |
| 66 | 3-chlorophenyl | —CH₂—N(tetrazol-1-yl) et —CH₂—N(tetrazol-2-yl) | Mixture of isomers MH⁺ = 607 tr₁ = 10.52 rt₂ = 10.99 |
| 67 | 3-chlorophenyl | (1H-tetrazol-5-yl)methyl | |
| 68 | 3-chlorophenyl | (tetrazolyl)methyl | |

TABLE 3

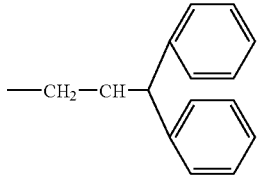

(IA)

| Compounds | $r_4, r'_4$ | $r_5, r'_5$ | $R_1$ | $R_2$ | Characterization Conditions m.p. ° C. |
|---|---|---|---|---|---|
| 69 | 4-Cl | 2,4-diCl | 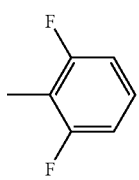 | H | m.p. = 116 |
| 70 | 4-OH | 2,4-diCl | 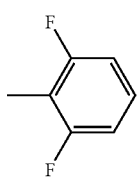 | H | m.p. = 196 |
| 71 | 4-OSO$_2$-nPr | 2,4-diCl | 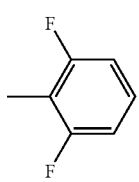 | H | m.p. = 77 |
| 72 | 4-OSO$_2$-nPr | 2,4-diCl | (same as above) | SO$_2$-nPr | m.p. = 153 |

The compounds of formula (I) possess very good affinity in vitro (IC$_{50}$≦5.10$^{-7}$M) for the CB$_1$ cannabinoid receptors, in the experimental conditions described by M. Rinaldi-Carmona et al. (FEBS Letters, 1994, 350, 240-244).

The antagonistic character of the compounds of formula (I) was demonstrated by the results obtained in the models of adenylate-cyclase inhibition as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The interaction of a compound according to the invention with the CB$_1$ receptors in the brain is determined in the mouse with the test of ex-vivo binding of [3H]-CP55940 after intravenous injection as described in M. Rinaldi-Carmona et al., FEBS Letters 1994, 350, 240-244 and M. Rinaldi-Carmona et al., Life Sciences 1995, 56, 1941-1947.

The interaction of a compound according to the invention with the CB$_1$ receptors in the periphery is determined in the mouse with the test of reversal of the inhibitory effect of CP55940 on gastrointestinal transit after oral administration as described in M. Rinaldi-Carmona et al., J. Pharmacol. Exp. Ther., 2004, 310, 905-914.

The toxicity of the compounds of formula (I) is compatible with their use as medication.

Thus, according to another of its aspects, the invention relates to medicinal products for human or veterinary medicine which contain a compound of formula (I), or a salt of addition of the latter to a pharmaceutically acceptable acid, or alternatively a solvate or a hydrate of the compound of formula (I).

Thus, the compounds according to the invention can be used in the treatment or prevention of diseases involving the CB$_1$ cannabinoid receptors, in humans or in animals notably in mammals, including without any limitation, dogs, cats, horses, cattle and sheep.

For example, without any limitation, the compounds of formula (I) can be used as psychotropic medicinal products, notably for the treatment of psychiatric disorders including anxiety, depression, mood disorders, insomnia, delusional disorders, obsessive disorders, psychoses in general, schizophrenia, attention deficit hyperactivity disorder (ADHD) in hyperactive children as well as for the treatment of disorders associated with the use of psychotropic substances, notably in the case of substance abuse and/or dependence on a substance, including alcohol addiction and nicotine addiction.

The compounds of formula (I) according to the invention can be used as medicinal products for the treatment of migraine, stress, diseases of psychosomatic origin, panic attacks, epilepsy, motor disorders, in particular dyskinesias or Parkinson's disease, tremor and dystonia.

The compounds of formula (I) according to the invention can also be used as medicinal products in the treatment of memory disorders, cognitive disorders, in particular in the treatment of senile dementias, of Alzheimer's disease, as well as in the treatment of attention or vigilance disorders.

Moreover, the compounds of formula (I) can be used as neuroprotectors, in the treatment of ischaemia, head injuries and the treatment of acute or chronic neurodegenerative diseases: including chorea, Huntington chorea, Tourette syndrome.

The compounds of formula (I) according to the invention can be used as medicinal products in the treatment of pain: neuropathic pain, acute peripheral pain, chronic pain of inflammatory origin, pain induced by anticancer treatment.

The compounds of formula (I) according to the invention can be used as medicinal products in human or veterinary medicine in the prevention and treatment of disorders of appetite, craving (for sugars, carbohydrates, drugs, alcohols or any appetizing substance) and/or eating disorders, notably for the treatment of obesity or of bulimia as well as for the treatment of type II diabetes or non-insulin-dependent diabetes and for the treatment of dyslipidemia, and of metabolic syndrome. Thus, the compounds of formula (I) according to the invention can be used in the treatment of obesity and of the risks associated with obesity, notably cardiovascular risks.

Moreover, the compounds of formula (I) according to the invention can be used as medicinal products in the treatment and prevention of gastrointestinal disorders, diarrhea, ulcers, vomiting, bladder and urinary disorders, liver diseases such as chronic cirrhosis, fibrosis, hepatic steatosis, steatohepatitis, as well as disorders of endocrine origin, cardiovascular disorders, hypotension and atherosclerosis, hemorrhagic shock, septic shock, asthma, chronic bronchitis, chronic obstructive pulmonary diseases, Raynaud's syndrome, glaucoma, fertility disorders, premature labor, abortion, inflammatory phenomena, immune system diseases, in particular autoimmune and neuroinflammatory such as rheumatoid arthritis, reactive arthritis, diseases resulting in demyelinization, multiple sclerosis, infectious and viral diseases such as encephalitis, cerebrovascular accidents and as medicinal products for anticancer chemotherapy, for the treatment of Guillain-Barré syndrome and for the treatment of bone diseases and osteoporosis.

According to the present invention, the compounds of formula (I) can be used quite particularly for the preparation of medicinal products for use in the prevention and treatment of psychotic disorders, in particular schizophrenia, attention deficit hyperactivity disorders (ADHD) in hyperactive children; for the prevention and treatment of memory disorders and cognitive disorders; for the treatment of alcohol dependence, nicotine dependence, for giving up drinking alcohol and smoking; acute or chronic neurodegenerative diseases.

More particularly, the compounds of formula (I) according to the present invention can be used in the treatment and prevention of disorders of appetite, metabolic disorders, gastrointestinal disorders, inflammatory phenomena, immune system diseases, psychotic disorders, alcohol dependence, and nicotine dependence.

According to one of its aspects, the present invention relates to the use of a compound of formula (I), its pharmaceutically acceptable salts and their solvates or hydrates for the treatment of the disorders and diseases stated above. According to another of its aspects, the present invention relates to pharmaceutical compositions containing, as active principle, a compound according to the invention. These pharmaceutical compositions contain an effective dose of at least one compound according to the invention, or a pharmaceutically acceptable salt, a solvate or hydrate of said compound or said salt, as well as at least one pharmaceutically acceptable excipient.

Said excipients are selected depending on the pharmaceutical form and the desired method of administration, from the usual excipients that are known by a person skilled in the art.

The pharmaceutical compositions according to the present invention can contain, alongside a compound of formula (I), one or more other active puinciple(s) that can be used in the treatment of the disorders and diseases stated above. Thus, the present invention also relates to pharmaceutical compositions containing a compound of formula (I) according to the present invention combined with one or more active principle(s) selected from one of the following therapeutic classes:

another antagonist of the CB$_1$ cannabinoid receptors;
a modulator of the CB$_2$ cannabinoid receptors;
an antagonist of the AT$_1$ angiotensin II receptors;
an inhibitor of the converting enzyme;
a calcium antagonist;
a diuretic;
a beta-blocker;
an antihyperlipaemic agent or an antihypercholesterolaemic agent;
an antidiabetic agent;
another anti-obesity agent or agent acting on metabolic disorders;
a nicotinic agonist, a partial nicotinic agonist;
an antidepressant, an antipsychotic, an anxiolytic;
an anticancer agent or antiproliferative agent;
an opioid antagonist;

as well as:

a memory-improving agent;
an agent for use in the treatment of alcoholism or of withdrawal symptoms;
an agent that can be used for treating osteoporosis;
a non-steroidal or steroidal anti-inflammatory drug;
an anti-infectious agent;
an analgesic;
an antiasthmatic agent.

"Antagonist of the AT$_1$ angiotensin II receptors" means a compound such as candesartan cilexetil, eprosartan, irbesartan, losartan potassium, olmesartan medoxomil, telmisartan, valsartan, and each of these compounds can itself be combined with a diuretic such as hydrochlorothiazide.

"Inhibitor of the converting enzyme" means a compound such as alacepril, benazepril, captopril, cilazapril, enalapril, enalaprilat, fosinopril, imidapril, lisinopril, moexipril, perindopril, quinapril, ramipril, spirapril, temocapril, trandolapril, zofenopril, and each of these compounds can itself be combined with a diuretic such as hydrochlorothiazide or indapamide or with a calcium antagonist such as amlodipine, diltiazem, felodipine or verapamil.

"Calcium antagonist" means a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline, verapamil.

"Beta-blocker" means a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertalol, tilisolol, timolol, xamoterol, xibenolol.

"Antihyperlipaemic or antihypercholesterolaemic agent" means a compound selected from the fibrates such as alufibrate, beclobrate, bezafibrate, ciprofibrate, clinofibrate, clofibrate, etofibrate, fenofibrate; the statins (HMG-CoA reductase inhibitors), such as atorvastatin, fluvastatin sodium, lovastatin, pravastatin, rosuvastatin, simvastatin, or a compound such as acipimox, aluminum nicotinate, azacosterol, cholestyramine, dextrothyroxine, meglutol, niceritrol, nicoclonate, nicotinic acid, beta-sitosterol, tiadenol.

"Antidiabetic agent" means a compound belonging to one of the following classes: sulfonylureas, biguanidines, alpha glucosidase inhibitors, thiazolidinediones, metiglinides, such as acarbose, acetohexamide, carbutamide, chlorpropamide, glibenclamide, glibomuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone, foliose, as well as insulin and insulin analogues.

"Other anti-obesity agent or agent acting on metabolic disorders" means a compound such as amfepramone, benfluorex, benzphetamine, indanorex, mazindol, mefenorex, methamphetamine, D-norpseudoephednine, sibutramine, a topiramate, a lipase inhibitor (orlistat cetilistat), a PPAR agonist (peroxisome proliferator activated receptor agonist), a dopamine agonist, a leptin receptor agonist, a serotonin reuptake inhibitor, a beta-3 agonist, a CCK-A agonist, an NPY inhibitor, an MC4 receptor agonist, an MCH (melanin concentrating hormone) receptor antagonist, an orexin antagonist, a phosphodiesterase inhibitor, an inhibitor of 11βHSD (11-β-hydroxy steroid dehydrogenase), a DPP-IV (dipeptidyl peptidase IV) inhibitor, an antagonist (or inverse agonist) of histamine H3, a CNTF (ciliary neurotrophic factor) derivative, a GHS (growth hormone secretagogue) receptor agonist, a ghrelin modulator, an inhibitor of diacylglycerol acyltransferase (DGAT), a phosphodiesterase (PDE) inhibitor, a thyroid hormone agonist, a glucocorticoid receptor antagonist, an inhibitor of stearoyl-CoA-desaturase (SCD), a modulator of transporters of phosphate, of glucose, of fatty acid, of dicarboxylate, a $5HT_2$ antagonist, a $5HT_6$ antagonist, a bombesine agonist.

"Opioid antagonist" means a compound such as naltrexone, naloxone or nalmefene.

"Agent for use in the treatment of alcoholism as well as withdrawal symptoms" means acamprosate, the benzodiazepines, beta-blockers, clonidine, carbamazepine.

"Agent for use in the treatment of osteoporosis" means for example the bisphosphonates such as etidronate, clodronate, tiludronate, risedronate. According to the present invention, it is also possible to combine other compounds having antihyperlipaemic, antihypercholesterolaemic, antidiabetic or anti-obesity properties. More particularly it is possible to combine compounds belonging to one of the following classes:

inhibitors of PTP 1B (protein tyrosine phosphase-1B), VPAC-2 receptor agonists, GLK modulators, retinoid modulators, inhibitors of glycogen phosphorylase (HGLPa), glucagon antagonists, glucose-6-phosphate inhibitors, activators of pyruvate dehydrogenase kinase (PKD), modulators of RXR, FXR, LXR, inhibitors of SGLT (sodium-dependent glucose transporter), inhibitors of CETP (cholesteryl ester transfer protein), inhibitors of squalene synthetase, inhibitors of squalene epoxidase, inhibitors of triglyceride synthesis, inducers of LDL (low-density lipoprotein) receptors, inhibitors of IBAT, inhibitors of FBPase (fructose-1,6-biphosphatase), modulators of CART (cocaine-amphetamine-regulated transcript), MC4 (melanocortin 4) modulators, orexin receptor antagonists.

According to another aspect of the invention, the compound of formula (I), one of its pharmaceutically acceptable salts or one of their solvates or hydrates and the other combined active principle can be administered simultaneously, separately or spread over time.

"Simultaneous use" means administration of the compounds of the composition according to the invention contained in one and the same pharmaceutical form.

"Separate use" means administration, at the same time, of the two compounds of the composition according to the invention each contained in a separate pharmaceutical form.

"Use spread over time" means the successive administration, of the first compound of the composition of the invention, contained in one pharmaceutical form, then of the second compound of the composition according to the invention, contained in a separate pharmaceutical form. In this case, the period of time that passes between administration of the first compound of the composition according to the invention and administration of the second compound of the same composition according to the invention does not generally exceed 24 hours.

In the pharmaceutical compositions of the present invention for oral, sublingual, subcutaneous, intramuscular, intravenous, topical, local, intratracheal, intranasal, transdermal or rectal administration, the active principle of formula (I) above, or optionally its salt, solvate or hydrate, can be administered in a unit form of administration, mixed with conventional pharmaceutical excipients, to animals and to human beings for the prophylaxis or treatment of the aforementioned disorders or diseases.

The appropriate unit forms of administration comprise the forms by the oral route such as tablets, soft or hard capsules, powders, granules and oral solutions or suspensions, forms for sublingual, buccal, intratracheal, intraocular, intranasal or inhalation administration, forms for topical, transdermal, subcutaneous, intramuscular or intravenous administration, forms for rectal administration, and implants. For topical application, the compounds according to the invention can be used in creams, gels, ointments or lotions.

As an example, a unit form of administration of a compound according to the invention in the form of a tablet can contain the following components:

| | |
|---|---|
| Compound according to the invention: | 50.0 mg |
| Mannitol: | 223.75 mg |
| Croscarmellose sodium: | 6.0 mg |
| Maize starch: | 15.0 mg |
| Hydroxypropylmethylcellulose: | 2.25 mg |
| Magnesium stearate: | 3.0 mg |

By the oral route, the dose of active principle administered per day can reach 0.01 to 100 mg/kg, in one or more doses, preferably 0.02 to 50 mg/kg.

There may be special cases where higher or lower doses are appropriate; such doses are still within the scope of the invention. In accordance with usual practice, the dosage appropriate to each patient is determined by the doctor depending on the method of administration, and the weight and response of said patient.

According to another of its aspects, the present invention also relates to a method of treatment of the pathologies stated above that comprises the administration, to a patient, of an effective dose of a compound according to the invention, or one of its pharmaceutically acceptable salts, or hydrates or solvates.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound corresponding to formula (I):

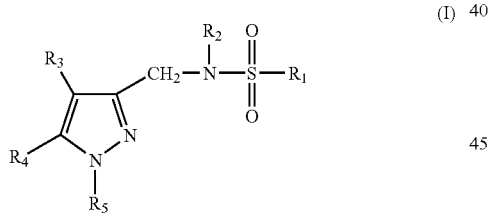

in which:

$R_1$ represents
- a $(C_1-C_{12})$alkyl, unsubstituted or substituted one or more times with substituents selected independently from a fluorine atom, a hydroxyl, a $(C_1-C_4)$alkoxy, a $(C_1-C_4)$alkylthio, a phenoxy, a trifluoromethoxy radical, a difluoromethoxy radical, a difluoromethylthio radical, a trifluoromethylthio radical;
- a non-aromatic $(C_3-C_{12})$ carbocyclic radical, unsubstituted or substituted one or more times with substituents selected independently from a $(C_1-C_4)$alkyl, a $(C_1-C_4)$alkoxy, a $(C_1-C_4)$alkylthio, a fluorine atom, a hydroxyl, a trifluoromethyl, difluoromethyl, trifluoromethoxy, difluoromethoxy, trifluoromethylthio, difluoromethylthio radical;
- a methyl a methyl substituted with a non-aromatic $(C_3-C_{12})$ carbocyclic radical, unsubstituted or substituted one or more times with substituents selected independently from a $(C_1-C_4)$alkyl, a $(C_1-C_4)$alkoxy, a $(C_1-C_4)$alkylthio, a fluorine atom, a hydroxyl, a trifluoromethyl, difluoromethyl, trifluoromethoxy, difluoromethoxy, trifluoromethylthio, difluoromethylthio radical;
- a phenyl, benzyl, benzhydryl, benzhydrylmethyl radical, in which each phenyl group is unsubstituted or substituted one or more times with substituents selected independently from a halogen atom, a hydroxyl, a methylenedioxy, a cyano, a nitro, a $(C_1-C_4)$alkylcarbonyl group or an Alk, OAlk, $S(O)_n$Alk or $OS(O)_n$Alk group;
- a phenyl radical substituted with a heterocyclic radical selected from pyrrolyl, imidazolyl, pyridyl or pyrazolyl, said heterocyclic radical being unsubstituted or substituted one or more times with one or more substituents selected independently from a halogen atom or a $(C_1-C_4)$alkyl group;
- a phenyl radical substituted with a phenyl or a phenoxy in which each phenyl group is unsubstituted or substituted one or more times with substituents selected independently from a halogen atom, a hydroxyl, a methylenedioxy, a cyano, a nitro, a $(C_1-C_4)$alkylcarbonyl group or an Alk, OAlk, $S(O)_n$Alk or $OS(O)_n$Alk group;
- a thienyl, furyl, oxazolyl, thiazolyl, imidazolyl, pyrrolyl, pyridyl radical, said radical being unsubstituted or substituted with one or more substituents selected independently from a halogen atom, a $(C_1-C_4)$alkyl, a trifluoromethyl group;
- a tetrahydronaphthalenyl or a naphthyl unsubstituted or substituted with one or more substituents selected independently from a halogen atom, a $(C_1-C_4)$alkyl, a di$(C_1-C_4)$alkylamino or a trifluoromethyl group;
- a 2,3-dihydrobenzofuranyl unsubstituted or substituted one or more times with a $(C_1-C_4)$alkyl group;
- an indol-2-yl or an N-methylindol-2-yl;

$R_2$ represents a hydrogen atom, a $(C_1-C_4)$alkyl or a $(C_1-C_4)$alkylsulphonyl group;

$R_3$ represents a cyano, a hydroxyl, a $(C_1-C_4)$alkoxy, a cyanomethyl, a hydroxymethyl, a $(C_1-C_4)$alkoxymethyl, a fluoromethyl, a tetrazolylmethyl, an N-(methyl)tetrazolylmethyl, a tetrazolyl, an N-(methyl)tetrazolyl, a $CONR_6R_7$ group, a $CH_2S(O)_n(C_1-C_4)$alkyl group, a $COOR_8$ group or a $CH_2NR_6R_7$ group;

$R_4$ and $R_5$ each represent independently a phenyl unsubstituted or substituted with one or more substituents selected independently from a halogen atom, a $(C_1-C_7)$ alkyl group unsubstituted or substituted one or more times with a fluorine atom, an OAlk, $S(O)_n$Alk or $OS(O)_n$Alk group;

$R_6$ and $R_7$ each represent independently a hydrogen atom or a $(C_1-C_4)$alkyl or $R_6$ and $R_7$ together with the nitrogen atom to which they are bound constitute a heterocyclic radical selected from pyrrolidinyl, piperidinyl, morpholinyl, piperazinyl unsubstituted or substituted one or more times with a $(C_1-C_4)$alkyl;

$R_8$ represents a $(C_1-C_4)$alkyl;

n represents 0, 1 or 2; and

Alk represents a $(C_1-C_4)$alkyl unsubstituted or substituted one or more times with a fluorine atom;

or a salt thereof or a hydrate or a solvate of said compound or said salt.

2. The compound of formula (I) according to claim 1 in which:
R$_1$ represents
 a (C$_1$-C$_7$)alkyl;
 a (C$_3$-C$_7$)cycloalkyl unsubstituted or substituted one or more times with a (C$_1$-C$_4$)alkyl group;
 a (C$_3$-C$_7$)cycloalkylmethyl unsubstituted or substituted one or more times on the carbocycle with a (C$_1$-C$_4$)alkyl;
 a phenyl unsubstituted or substituted with one or more substituents selected independently from a halogen atom, a (C$_1$-C$_4$)alkyl, a (C$_1$-C$_4$)alkoxy, a cyano, a trifluoromethyl group, a trifluoromethoxy group, an S(O)$_n$Alk group, a (C$_1$-C$_4$)alkylcarbonyl group, a phenyl;
 a benzyl unsubstituted or substituted with one or more substituents selected independently from a halogen atom, a (C$_1$-C$_4$)alkyl, a (C$_1$-C$_4$)alkoxy; a trifluoromethyl group;
 a thienyl, furyl, oxazolyl, thiazolyl, imidazolyl radical, said radical being unsubstituted or substituted with one or more substituents selected independently from a halogen atom, a (C$_1$-C$_4$)alkyl, a trifluoromethyl group;
 a naphthyl unsubstituted or substituted with one or more substituents selected independently from a (C$_1$-C$_4$)alkyl, a di(C$_1$-C$_4$)alkylamino;
 a 2,3-dihydrobenzofuranyl unsubstituted or substituted one or more times with a (C$_1$-C$_4$)alkyl group;
R$_2$ represents a hydrogen atom or a (C$_1$-C$_4$)alkyl;
R$_3$ represents a cyano, a hydroxyl, a (C$_1$-C$_4$)alkoxy, a cyanomethyl, a hydroxymethyl, a (C$_1$-C$_4$)alkoxymethyl, a fluoromethyl, a tetrazolylmethyl, an N-(methyl)tetrazolylmethyl, a tetrazolyl, an N-(methyl)tetrazolyl, a CONR$_6$R$_7$ group, a CH$_2$S(O)$_n$Alk group, a COOR$_8$ group;
R$_4$ and R$_5$ each represent independently a phenyl unsubstituted or substituted with one or more substituents selected independently from a halogen atom, a (C$_1$-C$_7$)alkyl, a (C$_1$-C$_4$)alkoxy, a trifluoromethyl group or an S(O)$_n$Alk group;
R$_6$ and R$_7$ each represent independently a hydrogen atom or a (C$_1$-C$_4$)alkyl or R$_6$ and R$_7$ together with the nitrogen atom to which they are bound constitute a heterocyclic radical selected from pyrrolidinyl, piperidinyl, morpholinyl, piperazinyl unsubstituted or substituted one or more times with a (C$_1$-C$_4$)alkyl;
R$_8$ represents a (C$_1$-C$_4$)alkyl;
n represents 0, 1 or 2; and
Alk represents a (C$_1$-C$_4$)alkyl;
or a salt thereof or a hydrate or a solvate of said compound or said salt.

3. The compound according to claim 1 of formula I in which R$_3$ is a cyano.

4. The compound according to claim 1 of formula I in which R$_3$ is a hydroxyl.

5. The compound according to claim 1 of formula I in which R$_3$ is a (C$_1$-C$_4$)alkoxy.

6. The compound according to claim 1 of formula I in which R$_3$ is a (C$_1$-C$_4$)alkoxymethyl.

7. The compound according to claim 1 of formula I in which R$_3$ is a CONR$_6$R$_7$ group.

8. The compound according to claim 1 of formula I in which R$_3$ is a COOR$_8$.

9. The compound according to claim 1 of formula I in which R$_3$ is a tetrazol-1-ylmethyl or a tetrazol-2-ylmethyl.

10. The compound according to claim 1 of formula I in which:
R$_1$ represents:
 a phenyl, benzyl, benzhydryl, benzhydrylmethyl radical, in which each phenyl group is unsubstituted or substituted one or more times with substituents selected independently from a halogen atom, a hydroxyl, a (C$_1$-C$_4$)alkyl, a (C$_1$-C$_4$)alkoxy, a methylenedioxy, a cyano, a nitro, a trifluoromethyl, a difluoromethyl, a difluoromethoxy, a trifluoromethoxy, a trifluoromethylthio, a difluoromethylthio, an S(O)$_n$Alk group, an OS(O)$_n$Alk group, a (C$_1$-C$_4$)alkylcarbonyl group;
 a furyl radical unsubstituted or substituted with one or more substituents selected independently from a halogen atom, a (C$_1$-C$_4$)alkyl, a trifluoromethyl group;
R$_2$ represents a hydrogen atom or a (C$_1$-C$_4$)alkylsulphonyl group;
R$_3$ represents a cyano, a hydroxyl, a (C$_1$-C$_4$)alkoxy, a hydroxymethyl, a (C$_1$-C$_4$)alkoxymethyl, a CONR$_6$R$_7$ group, a COORS group, a tetrazol-1-yl methyl or a tetrazol-2-ylmethyl, the groups R$_6$, R$_7$, R$_8$ being as defined for (I);
R$_4$ represents a 4-chlorophenyl, a 4-methoxyphenyl or a 4-OSO$_2$-Alk, Alk representing a (C$_1$-C$_4$)alkyl unsubstituted or substituted one or more times with a fluorine atom; and
R$_5$ represents a 2-chlorophenyl, a 2-bromophenyl or a 2,4-dichlorophenyl;
or a salt thereof or a hydrate or a solvate of said compound or said salt.

11. The compound according to claim 1 of formula I in which:
R$_1$ represents a 3-chlorophenyl, 3-fluorophenyl, 3,6-difluorophenyl, 2,6-difluorophenyl, 3-methoxyphenyl, 3-trifluoromethylphenyl, 3-trifluoromethoxyphenyl, a benzyl, a 4-trifluoromethylbenzyl or a 2-trifluoromethyl-4-methylfuryl group;
R$_2$ represents a hydrogen atom;
R$_3$ represents a cyano, methoxy or dimethylaminocarbonyl group;
R$_4$ represents a 4-chlorophenyl, a 4-methoxy or a 4-propanesulphonyloxy; and
R$_5$ represents a 2,4-dichlorophenyl or a 2-chlorophenyl;
or a salt thereof or a hydrate or a solvate of said compound or said salt.

12. The compound according to claim 1, selected from:
 —N-{[5-(4-chlorophenyl)-4-cyano-1-(2,4-dichlorophenyl)-1H-pyrazol-3-yl]methyl}-3-cyanobenzenesulfonamide,
 —N-{[5-(4-chlorophenyl)-4-cyano-1-(2,4-dichlorophenyl)-1H-pyrazol-3-yl]methyl}-3-trifluorobenzenesulfonamide,
 —N-{[5-(4-chlorophenyl)-4-cyano-1-(2,4-dichlorophenyl)-1H-pyrazol-3-yl]methyl}-2-trifluoromethoxybenzenesulfonamide,
 —N-{[5-(4-chlorophenyl)-4-cyano-1-(2,4-dichlorophenyl)-1H-pyrazol-3-yl]methyl}-3-methoxybenzenesulfonamide,
 —N-{[5-(4-chlorophenyl)-4-cyano-1-(2,4-dichlorophenyl)-1H-pyrazol-3-yl]methyl}-3-chlorobenzenesulfonamide,
 —N-{[5-(4-chlorophenyl)-4-cyano-1-(2-chlorophenyl)-1H-pyrazol-3-yl]methyl}-3-fluorobenzenesulfonamide,
 —N-{[5-(4-chlorophenyl)-4-cyano-1-(2-chlorophenyl)-1H-pyrazol-3-yl]methyl}-2-fluorobenzenesulfonamide, —N-{[5-(4-chlorophenyl)-4-cyano-1-(2-chlorophenyl)-1H-pyrazol-3-yl]methyl}-2-trifluoromethoxybenzenesulfonamide, —N-{[5-(4-methoxyphenyl)-4-cyano-1-(2,4-dichlorophenyl)-1H-pyrazol-3-yl]methyl}-3,5-difluorobenzenesulfonamide, —N-{[5-(4-chlorophenyl)-4-methoxy-1-(2,4-dichlorophenyl)-1H-pyrazol-3-yl]methyl}-3-chlorobenzenesulfonamide, -5-(4-chlorophenyl)-3-({[(3-chlorophenyl)sulfonyl]amino}methyl)-1-(2,4-dichlorophenyl)-N-methyl-1H-pyrazole-4-carboxamide, —N-{[5-(4-chlorophenyl)-4-cyano-1-(2,4-dichlorophenyl)-1H-pyrazol-3-yl]methyl}-1-phenylmethanesulfonamide, and —N-{[5-(4-chlorophenyl)-4-cyano-1-(2,4-dichlorophenyl)-1H-pyrazol-3-yl]methyl}-5-methyl-2-(trifluoromethyl)furan-3-sulfonamide;

or a salt thereof or a hydrate or a solvate of said compound or said salt.

13. A method of preparation of a compound of formula (I) according to claim 1, comprising reacting a compound of formula (II):

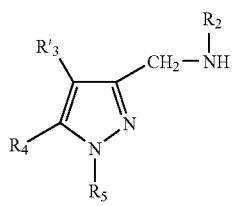

(II)

in which $R_2$, $R_4$, $R_5$ are as defined for a compound of formula (I) and $R'_3$ represents $R_3$ or a precursor of $R_3$, in the presence of a base, in a solvent, with a sulfonyl halide of formula $HalSO_2R_1$, in which $R_1$ is as defined for a compound of formula (I) in claim 1 and Hal represents a halogen atom; and if applicable, the compound obtained of formula:

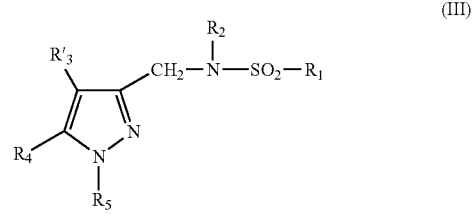

(III)

in which $R'_3$ is $R_3$ or is a precursor of $R_3$, is converted to a compound of formula (I).

14. A pharmaceutical composition comprising a compound of formula (I) according to claim 1, or a pharmaceutically acceptable salt thereof, or a hydrate or a solvate of said compound or said salt, in combination with at least one pharmaceutically acceptable excipient.

15. A pharmaceutical composition comprising a compound of formula (I) according to claim 12, or a pharmaceutically acceptable salt thereof, or a hydrate or a solvate of said compound or said salt, in combination with at least one pharmaceutically acceptable excipient.

* * * * *